United States Patent [19]
Elliott et al.

[11] Patent Number: 5,747,466
[45] Date of Patent: May 5, 1998

[54] 3-DEOXY-3-DESCLADINOSE DERIVATIVES OF ERYTHROMYCINS A AND B

[75] Inventors: Richard L. Elliott, Grayslake; Yat Sun Or, Libertyville; Daisy Pireh, Lincolnshire, all of Ill.; Daniel T. Chu, Santa Clara, Calif.

[73] Assignee: Abbott Laboratories, Abbott Park, Ill.

[21] Appl. No.: 729,269

[22] Filed: Oct. 10, 1996

Related U.S. Application Data

[60] Provisional application No. 60/006,432 Nov. 8, 1995.
[51] Int. Cl.$^6$ .............................. A61K 31/70; C07H 17/08
[52] U.S. Cl. .............................. 514/29; 536/7.2; 536/7.3; 536/7.4
[58] Field of Search .............................. 536/72, 7.3, 7.4; 579/29

[56] References Cited

U.S. PATENT DOCUMENTS

| 4,331,803 | 5/1982 | Watanabe et al. ............ 536/7.2 |
| 5,141,926 | 8/1992 | Weber et al. ............ 514/29 |
| 5,403,923 | 4/1995 | Kashimura et al. ............ 536/7.4 |

FOREIGN PATENT DOCUMENTS

| 0487411 | 5/1992 | European Pat. Off. |
| 0487411A | 5/1992 | European Pat. Off. |
| 0596802 | 5/1994 | European Pat. Off. |
| 2697524 | 5/1994 | European Pat. Off. |
| 0619319A | 10/1997 | European Pat. Off. |
| 9321200 | 10/1993 | WIPO |

OTHER PUBLICATIONS

Journal of Medicinal Chemistry, vol. 17 (1974), pp. 953–956, R. A. LeMahieu, et al. "Glycoside Cleavage Reactions on Erythromycin A. Preparation of Erythromycin A".

*Primary Examiner*—Elli Peselev
*Attorney, Agent, or Firm*—Mona Anand

[57] ABSTRACT

A compound selected from the group:

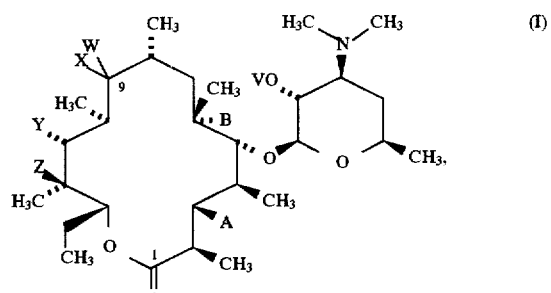

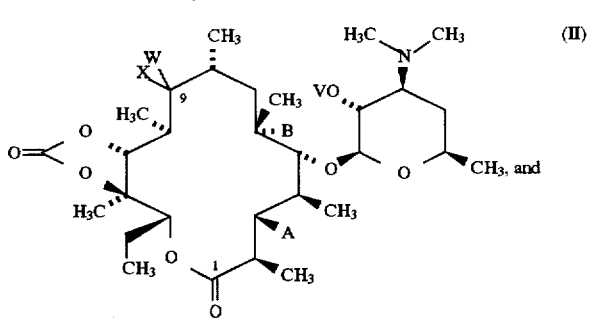

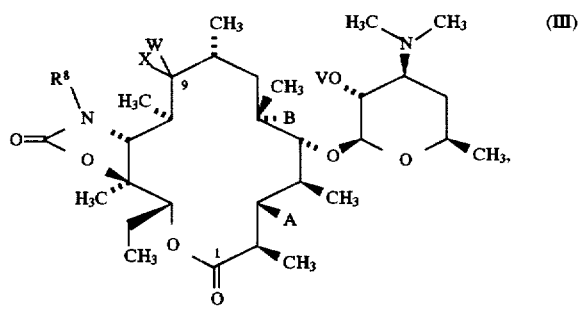

wherein A, B, V, W, X and $R^8$ are specifically defined; pharmaceutical compositions thereof; a method of treating or preventing bacterial infections by administering therapeutically effective pharmaceutical compositions thereof; and a process for the preparation thereof.

18 Claims, No Drawings

3-DEOXY-3-DESCLADINOSE DERIVATIVES OF ERYTHROMYCINS A AND B

CROSS REFERENCE TO RELATED APPLICATIONS

This application claims benefit of U.S. Provisional Application No. 60/006,432, filed Nov. 8, 1995.

TECHNICAL FIELD

The present invention relates to novel semisynthetic macrolides having antibacterial activity and useful in the treatment and prevention of bacterial infections. More particularly, the invention relates to 3-deoxy-3-descladinose-derivatives of erythromycin A and B, compositions containing such compounds and methods for using the same.

BACKGROUND OF THE INVENTION

Erythromycins A through D, represented by formula (E),

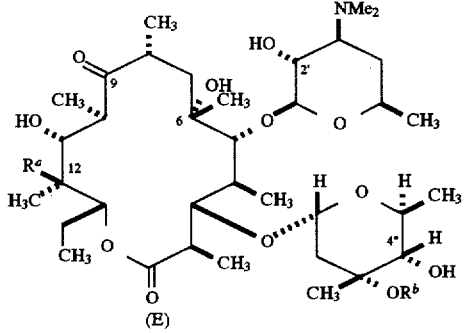

| Erythromycin | $R^a$ | $R^b$ |
|---|---|---|
| A | —OH | —CH$_3$ |
| B | —H | —CH$_3$ |
| C | —OH | —H |
| D | —H | —H | are well-known and potent antibacterial agents, used widely to treat and prevent bacterial infection. As with other antibacterials, however, bacterial strains having resistance or insufficient susceptibility to erythromycin have been identified. Therefore, there is a continuing need to identify new antibiotic compounds to which resistance has not developed. Also, new antibiotics having less potential to developing resistance are desired. Consequently, numerous investigators have prepared chemical derivatives of erythromycin in an attempt to obtain analogs having modified or improved profiles of antibiotic activity.

Erythromycin analogs having modifications at the C-3 or C-6 position have been disclosed in U.S. Pat. No. 5,403,923, issued Apr. 4, 1995, European application EP 487411, published May 27, 1992, French Patent Number 2,697,524, issued May 6, 1994, European application EP 596802, published May 11, 1994, PCT application WO 9321200, published Oct. 28, 1993, U.S. Pat. No. 4,331,803, issued May 25, 1982, and U.S. Pat. No. 5,141,926, issued Aug. 25, 1992.

SUMMARY OF THE INVENTION

The present invention provides a novel class of 3-deoxy-3-descladinose derivatives of erythromycins A and B which possess antibacterial activity.

In one aspect of the present invention are disclosed novel derivatives of erythromycin, as well as the pharmaceutically acceptable salts and esters thereof, having a formula selected from the group:

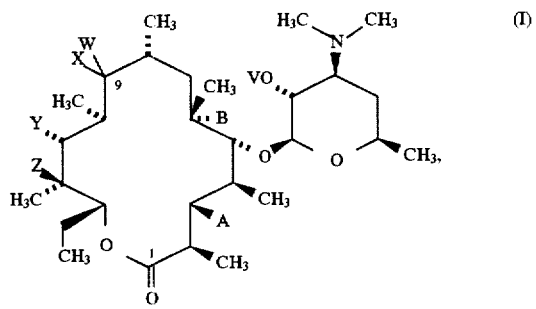

wherein:

A is hydrogen, —O(C=S)—SR$^1$, or —O(C=S)—OR$^1$, wherein R$^1$ is selected from the group consisting of:
  (a) C$_1$-C$_6$-alkyl,
  (b) aryl-C$_1$-C$_6$-alkyl,
  (c) substituted aryl-C$_1$-C$_6$-alkyl,
  (d) aryl, or
  (e) heteroaryl;

B is selected from the group consisting of hydrogen, hydroxy, and methoxy;

V is hydrogen or a hydroxy-protecting group;

W is hydrogen; and X is selected from the group consisting of:
  (a) NR$^2$R$^3$, wherein R$^2$ and R$^3$ are independently selected from the group consisting of hydrogen, C$_1$-C$_6$-alkyl, C$_1$-C$_6$-alkylamino, aryl-C$_1$-C$_6$-alkyl, or heteroaryl-C$_1$-C$_6$-alkyl, or wherein R$^2$ and R$^3$ are taken together with the nitrogen atom to which they are attached to form a 5-to-7-membered saturated ring; and
  (b) NR$_4$—(C=O)—R$^1$, wherein R$^1$ is as described above and R$^4$ is hydrogen or C$_1$-C$_6$-alkyl; or W and X are taken together and represent =O, =N—O—R$^2$, wherein R$^2$ is as described above, or =N—R$^5$, wherein R$^5$ is selected from the group consisting of:
  (a) hydrogen,
  (b) C$_1$-C$_6$-alkyl,
  (c) substituted C$_1$-C$_6$-alkyl,
  (d) —(CH$_2$)$_m$—L—(CH$_2$)$_n$—M—CH$_2$—H, wherein m=1–6, n=1–6, L and M are both oxygen, L is oxygen and M is absent, or M is oxygen and L is absent,
  (e) —(CH$_2$)$_m$—L—aryl-M—(CH$_2$)$_n$—H, wherein m=1–6, n=1–6, L and M are both oxygen, L is oxygen and M is absent, or M is oxygen and L is absent, and
  (f) —(CH$_2$)$_m$L—(CH$_2$)$_n$—M-aryl-H, wherein m=1–6, n=1–6, L and M are both oxygen, L is oxygen and M is absent, or M is oxygen and L is absent;

Y is —OH, or —OR$^6$ wherein R$^6$ is a hydroxy-protecting group; and

Z is hydrogen, —OH, or —OR$^7$ wherein R$^7$ is a hydroxy-protecting group;

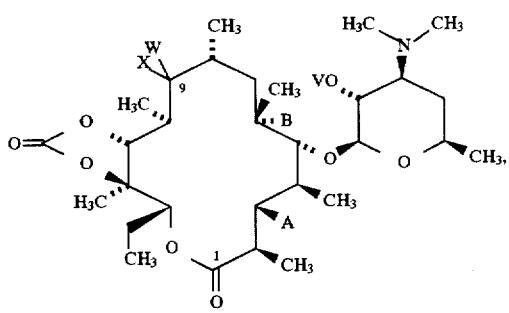

wherein A, B, V, W, and X are as defined above, or

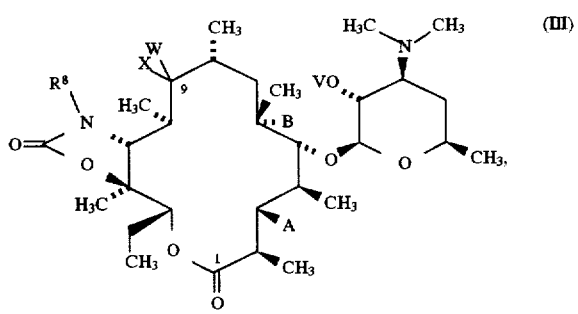

wherein A, B, V, W, and X are as defined above, and $R^8$ is selected from the group consisting of:
(a) hydrogen,
(b) $C_1$–$C_6$-alkyl,
(c) aryl,
(d) aryl-$C_1$–$C_6$-alkyl,
(e) heteroaryl-$C_1$–$C_6$-alkyl,
(f) cycloalkyl,
(g) cycloalkyl-$C_1$–$C_6$-alkyl,
(h) —NH—$R^9$, wherein $R^9$ is selected from the group consisting of:
 (aa) $C_1$–$C_6$-alkyl,
 (bb) aryl-$C_1$–$C_6$-alkyl,
 (cc) heteroaryl-$C_1$–$C_6$-alkyl,
 (dd) $C_3$–$C_7$-cycloalkyl,
 (ee) $C_3$–$C_7$-cycloalkyl-$C_1$–$C_6$-alkyl,
 (ff) —CO—$C_1$–$C_6$-alkyl,
 (gg) —CO-aryl,
 (hh) —CO—$C_1$–$C_6$-alkyl-aryl-; and
(i) —N=CH—$R^{10}$, wherein $R^{10}$ is selected from the group consisting of:
 (aa) $C_1$–$C_6$-alkyl,
 (bb) aryl,
 (cc) aryl-$C_1$–$C_6$-alkyl,
 (dd) heteroaryl-$C_1$–$C_6$-alkyl,
 (ee) $C_3$–$C_7$-cycloalkyl, and
 (ff) $C_3$–$C_7$-cycloalkyl-$C_1$–$C_6$-alkyl.

In a second aspect of the present invention are disclosed pharmaceutical compositions comprising a therapeutically effective amount of the above compounds in combination with a pharmaceutically acceptable carrier.

In a further aspect of the invention, a method for treating or preventing bacterial infections in a patient in need of such treatment or prevention is disclosed, comprising administering to the patient a therapeutically effective amount of one of the above compounds.

Also one aspect of the invention includes processes for the preparation of the compounds of the invention.

DETAILED DESCRIPTION OF THE INVENTION

The term "$C_1$–$C_6$-alkyl", as used herein, refers to saturated, straight- or branched-chain hydrocarbon radicals containing from one to six carbon atoms including, but not limited to, methyl, ethyl, propyl, isopropyl, n-butyl, tert-butyl, neopentyl and n-hexyl, or to a mono-unsaturated straight- or branched-chain hydrocarbon radicals containing from three to six carbon atoms including, but not limited to, propenyl, n-butenyl, and n-hexenyl.

The term "$C_1$–$C_6$-alkylamino", as used herein, refers to an amino radical having appended thereto one or two $C_1$–$C_6$-alkyl radicals as defined above, such as for example methylamino, dimethyl amino, ethylamino, diethylamino and butylamino.

The term "$C_1$–$C_6$-alkylamino-$C_1$–$C_6$-alkyl", as used herein, refers to a $C_1$–$C_6$-alkyl radical having appended thereto, by replacement of a hydrogen atom, a $C_1$–$C_6$-alkylamino radical, as defined above.

The term "aryl", as used herein, refers to an unsubstituted carbocyclic aromatic radical, including, for example, phenyl and 1- or 2-naphthyl.

The term "aprotic solvent" as used herein refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th edition, edited by John A. Riddick, et al., Vol. II, in the Techniques of Chemistry Series, John Wiley & Sons, N.Y., 1986.

The term "aryl-$C_1$–$C_6$-alkyl", as used herein, refers to a $C_1$–$C_6$-alkyl radical having appended thereto, by replacement of a hydrogen atom, an aryl radical, as defined above.

The term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

The term "heteroaryl-$C_1$–$C_6$-alkyl", as used herein, refers to a $C_1$–$C_6$-alkyl radical having appended thereto, by replacement of a hydrogen atom, a heteroaryl radical as defined above.

The term "hydroxy-protecting group", as used herein, refers to an easily removable group to which are known in the art to protect a hydroxyl group against undesirable reaction during synthetic procedures and to be selectively removable. The use of hydroxy-protecting groups is well known in the art for protecting groups against undesirable reactions during a synthetic procedure and many such protecting groups are known, cf, for example, T. H. Greene and P. G. M. Wuts, *Protective Groups in Organic Synthesis*, 2nd edition, John Wiley & Sons, New York (1991). Examples of hydroxy-protecting groups include, but are not limited to, methylthiomethyl, tert-dimethylsilyl, tert-butyldiphenylsilyl, acyl substituted with an aromatic group and the like.

The term "protected-hydroxy" refers to a hydroxy group protected with a hydroxy protecting group, as defined above, including benzoyl, acetyl, trimethylsilyl, triethylsilyl, methoxymethyl groups, for example.

The term "substituted $C_1$–$C_6$-alkyl", as used herein, refers to a $C_1$–$C_6$-alkyl radical as defined above wherein one, two or three of the hydrogen atoms thereon have been independently replaced with a Cl, Br, F, OH, methoxy, ethoxy, propoxy, amino, $C_1$–$C_6$-alkylamino, as defined below, or $C_1$–$C_6$-alkylamino-$C_1$–$C_6$-alkyl, as defined below, group.

The term "substituted-aryl", as used herein, refers to an aryl radical having appended thereto by independent replacement of one, two or three of the hydrogen atoms thereon with Cl, Br, F, OH, methoxy, ethoxy, propoxy, $C_1$–$C_6$-alkyl, trifluoromethyl or methoxymethyl groups.

The term "substituted aryl-$C_1$–$C_6$-alkyl", as used herein, refers to refers to a $C_1$–$C_6$-alkyl radical having appended thereto, by replacement of a hydrogen atom, an substituted aryl radical, as defined above.

Compound of Formula (III) wherein: A=H; B=methoxy; V=H; W and X taken together are =O; $R^8$=$NH_2$;

Compound of Formula (I) wherein: A=H; B=hydroxy; V=H; W and X taken together are =O; Y=Z=—OH;

Compound of Formula (III) wherein: A=H; B=methoxy; V=H; W and X taken together are =O; $R^8$=—NH—CO—$CH_3$;

Compound of Formula (III) wherein: A=H; B=methoxy; V=H; W and X taken together are =O; $R^8$=—N=CH-phenyl;

Compound of Formula (III) wherein: A=H; B=methoxy; V=H; W and X taken together are =O; $R^8$=—$NH_2$—$CH_2$-phenyl;

Compound of Formula (III) wherein: A=H; B=methoxy; V=H; W and X taken together are =O; $R^8$=—$CH_2$—$CH_2$—$CH_2$-phenyl;

Compound of Formula (III) wherein: A=H; B=methoxy; V=H; W and X taken together are O; $R^8$=NH—CO—$C_6H_5$;

Compound of Formula (III) wherein: A=H; B=methoxy; V=H; W and X taken together are O; $R^8$=NH—CO—$CH_2$—$C_6H_5$;

Compound of Formula (III) wherein: A=H; B=methoxy; V=H; W and X taken together are O; $R^8$=NH—CO—$CH_2CH_2C_6H_5$;

Compound of Formula (III) wherein: A=H; B=methoxy; V=H; W and X taken together are O; $R^8$=NH—CO—$CH_2$—$CH_2$—$C_6H_5$;

Compound of Formula (III) wherein: A=H; B=methoxy; V=H; W and X taken together are O; $R^8$=NH—CO—$CH_2$—COOMe;

Compound of Formula (III) wherein: A=H; B=methoxy; V=H; W and X taken together are O; $R^8$=NH—CO—$CH_2$—$CH_2$-(4-quinoyl);

Compound of Formula (III) wherein: A=H; B=methoxy; V=H; W and X taken together are O; $R^8$=N=CH—$CH_3$;

Compound of Formula (III) wherein: A=H; B=methoxy; V=H; W and X taken together are O; $R^8$=N=CH—$CH_2C_6H_5$;

Compound of Formula (III) wherein: A=H; B=methoxy; V=H; W and X taken together are O; $R^8$=N=CH—$CH_2CH_2C_6H_5$;

Compound of Formula (III) wherein: A=H; B=methoxy; V=H; W and X taken together are O; $R^8$=N=CH—CH=CH-phenyl;

Compound of Formula (III) wherein: A=H; B=methoxy; V=H; W and X taken together are O; $R^8$=N=CH—$CH_2$—$CH_2$-(4-quinoyl);

Compound of Formula (III) wherein: A=H; B=methoxy; V=H; W and X taken together are O; $R^8$=N=CH-cyclopentane;

In one embodiment of the invention are compounds of Formula (I) above, wherein A, B, V, W, X, Y and Z are as defined above.

In a second embodiment of the invention are compounds of Formula (II) above, wherein A, B, V, W, and X are as defined above.

In another embodiment of the invention are compounds of Formula (III) above, wherein A, B, V, W, X and $R^8$ are as defined above.

In a preferred embodiment of the invention are compounds of Formula (III) above, wherein A, B, V, W, X and $R^8$ are as defined above, and $R^8$ is —NH—$R^9$, wherein $R^9$ is selected from the group consisting of:

(aa) $C_1$–$C_6$-alkyl,
(bb) aryl-$C_1$–$C_6$-alkyl,
(cc) heteroaryl-$C_1$–$C_6$-alkyl,
(dd) $C_3$–$C_7$-cycloalkyl,
(ee) $C_3$–$C_7$-cycloalkyl-$C_1$–$C_6$-alkyl,
(ff) —CO—$C_1$–$C_6$-alkyl,
(gg) —CO-aryl, and
(hh) —CO—$C_1$–$C_6$-alkyl-aryl-.

In another embodiment of the invention are compounds of Formula (I) above wherein A is hydrogen and Z is —OH or —O—$R^7$.

Representative compounds of the invention include:
Compound of Formula (I) wherein: A=H; B=methoxy; V=H; W and X taken together are =O; Y=Z=—OH;

Compound of Formula (I) wherein: A=H; B=methoxy; V=H; W and X taken together are =N—OH; Y=Z=—OH;

Compound of Formula (II) wherein: A=H; B=methoxy; V=H; W and X taken together are =O;

Compound of Formula (III) wherein: A=H; B=methoxy; V=H; W and X taken together are =O; $R^8$=—$CH_2$—$CH_2$—$CH_2$—$CH_2$-phenyl;

Compound of Formula (III) wherein: A=H; B=methoxy; V=H; W and X taken together are =O; $R^8$=—$CH_2$—$CH_2$-phenyl-4-O-phenyl;

Compound of Formula (I) wherein: A=H; B=methoxy; V=H; W and X taken together are =N—O—$CH_3$; Y=Z=—OH;

Compound of Formula (I) wherein: A=H; B=methoxy; V=H; W and X taken together are =N—O—$CH_2$—$CH_3$; Y=Z=—OH; and Compound of Formula (I) wherein: A=H; B=methoxy; V=H; W and X taken together are =N—O—$CH_2$—O—$CH_2$—$CH_2$—O—$CH_3$; Y=Z=—OH;

Compound of Formula (III) wherein: A=H; B=methoxy; V=H; W and X taken together are O, $R^8$=N=CH—$CH_2$-cyclohexane;

Compound of Formula (III) wherein: A=H; B=methoxy; V=H; W and X taken together are O; $R^8$=NH-ethyl;

Compound of Formula (III) wherein: A=H; B=methoxy; V=H; W and X taken together are O; $R^8$=NH—$CH_2C_6H_5$;

Compound of Formula (III) wherein: A=H; B=methoxy; V=H; W and X taken together are O; $R^8$=NH—;

Compound of Formula (III) wherein: A=H; B=methoxy; V=H; W and X taken together are O; $R^8$=NH—$CH_2$—$CH_2$—$CH_2$—$C_6H_5$;

Compound of Formula (III) wherein: A=H; B=methoxy; V=H; W and X taken together are O; $R^8$=NH—$CH_2$—CH=CH-phenyl;

Compound of Formula (III) wherein: A=H; B=methoxy; V=H; W and X taken together are O; $R^8$=NH—$CH_2$—$CH_2$—$CH_2$-(4-quinoyl);

Compound of Formula (III) wherein: A=H; B=methoxy; V=H; W and X taken together are O; $R^8$=NH—CH—$CH_2$-cyclohexane;

Compound of Formula (III) wherein: A=H; B=methoxy; V=H; W and X taken together are O; $R^8$=H;

Compound of Formula (III) wherein: A=H; B=methoxy; V=H; W and X taken together are O; $R^8$=Me;

Compound of Formula (III) wherein: A=H; B=methoxy; V=H; W and X taken together are O; $R^8$=benzyl;

Compound of Formula (III) wherein: A=H; B=methoxy; V=H; W and X taken together are O; $R^8$=phenylethyl;

Compound of Formula (III) wherein: A=H; B=methoxy; V=H; W and X taken together are O; $R^8$=phenylpropyl;

Compound of Formula (III) wherein: A=H; B=methoxy; V=H; W and X taken together are O; $R^8$=—$CH_2$—$CH_2$—$CH_2$—$CH_2$-(4-quinoyl);

Compound of Formula (III) wherein: A=H; B=methoxy; V=H; W and X taken together are O; $R^8$=cyclohexyl;

Compound of Formula (III) wherein: A=H; B=methoxy; V=H; W and X taken together are O; $R^8$=—$CH_2$—$CH_2$-cyclohexyl; and Compound of Formula ((III) wherein) wherein: A=H; B=methoxy; V=H; W and X taken together are =O; $R^8$=phenyl.

Selected representative compounds of the invention include:

Compound of Formula (I) wherein: A=H; B=methoxy; V=H; W and X taken together are =O; Y=Z=—OH;

Compound of Formula (I) wherein: A=H; B=methoxy; V=H; W and X taken together are =N—OH; Y=Z=—OH;

Compound of Formula (II) wherein: A=H; B=methoxy; V=H; W and X taken together are =O;

Compound of Formula (III) wherein: A=H; B=methoxy; V=H; W and X taken together are =O; $R^8$=—$CH_2$—$CH_2$—$CH_2$—$CH_2$-phenyl;

Compound of Formula (III) wherein: A=H; B=methoxy; V=H; W and X taken together are =O; $R^8$=—$CH_2$—$CH_2$-phenyl-4-O-phenyl;

Compound of Formula (I) wherein: A=H; B=methoxy; V=H; W and X taken together are =N—O—$CH_3$; Y=Z=—OH;

Compound of Formula (I) wherein: A=H; B=methoxy; V=H; W and X taken together are =N—O—$CH_2$—$CH_3$; Y=Z=—OH; and Compound of Formula (I) wherein: A=H; B=methoxy; V=H; W and X taken together are =N—O—$CH_2$—O—$CH_2$—$CH_2$—O—$CH_3$; Y=Z=—OH.

One object of the present invention is to provide a process for the preparation of 3-deoxy-3-descladinose derivatives of erythromycins A and B having the formula:

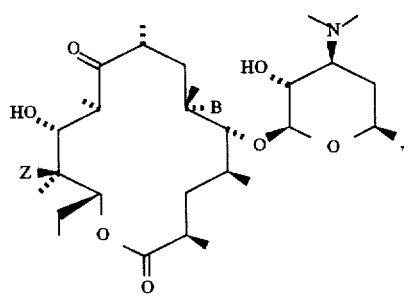

wherein B is hydrogen, hydroxy or methoxy, and Z is H or OH, the method comprising:

(a) reacting a compound having the formula:

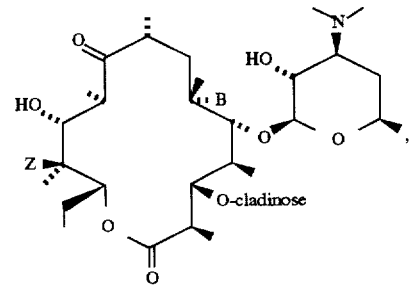

wherein B, and Z are as defined above, with a strong acid, preferably 0.5–1.5N HCl or dichloroacetic acid, in a suspension in aqueous alcohol, preferably, methanol, ethanol, or isopropanol, by stirring at ambient temperature for 0.5 to 24 hours to give a first intermediate compound having the formula:

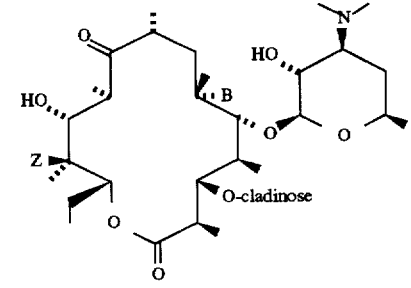

wherein B, and Z are as defined above;

(b) reacting the first intermediate compound with an excess of NaH at from 0° to −30° C. under an inert atmosphere, in an aprotic solvent such as DMF, THF, or $Et_2O$, for example, followed by reaction of the intermediate anion with $CS_2$ and $CH_3I$ at −5° to 10° C., to form a second intermediate 3-O-xanthyl compound having the formula:

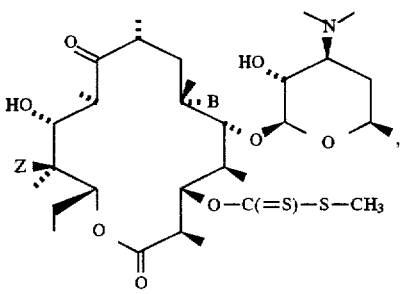

wherein B, and Z are as defined above;

(c) reacting the second intermediate compound with 1.1–1.3 equivalents of Bu₃SnH under an inert atmosphere in the presence of a catalytic amount of AIBN or other suitable radical initiator, in a solvent suitable for a free radical reaction, such as benzene or toluene, for example, at reflux conditions, and in the case wherein B=OH and M=NOR², followed by deoximation with, for example, NaNO₂ in the presence of aq. acid/MeOH, or using NaHSO₃/formic acid in H₂O/isopropanol at r.t to reflux to afford the desired compound.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 66: 1–19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than six carbon atoms. Examples of particular esters includes formates, acetates, propionates, butyates, acrylates and ethylsuccinates.

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), bucally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or lower mammal by administering to the patient a therapeutically effective amount of a compound of the invention, in such amounts and for such time as is necessary to achieve the desired result. By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

Numerous asymmetric centers may exist in the compounds of the present invention. Except where otherwise noted, the present invention contemplates the various stereoisomers and mixtures thereof. Accordingly, whenever a bond is represented by a wavy line, it is intended that a mixture of stereo-orientations or an individual isomer of assigned or unassigned orientation may be present.

ABBREVIATIONS

Abbreviations which may have been used in the descriptions of the scheme and the examples that follow are: AIBN for azobisisobutyronitrile; $Bu_3SnH$ for tributyltin hydride; CDI for carbonyldiimidazole; DBU for 1,8-diazabicyclo-[5.4.0]undec-7-ene; DEAD for diethylazodicarboxylate; DMF for dimethyl formamide; DPPA for diphenylphosphoryl azide; EtOAc for ethyl acetate; MeOH for methanol; $NaN(TMS)_2$ for sodium bis(trimethylsilyl)amide; NMMO for N-methyl-morpholine N-oxide; TEA for triethylamine; THF for tetrahydrofuran; TPP for triphenylphosphine.

SYNTHETIC METHODS

The compounds and processes of the present invention will be better understood in connection with the following synthetic schemes which illustrate the methods by which the compounds of the invention may be prepared. The groups A, B, V, W, X, Y and Z are as defined above unless otherwise noted below.

SCHEME 1

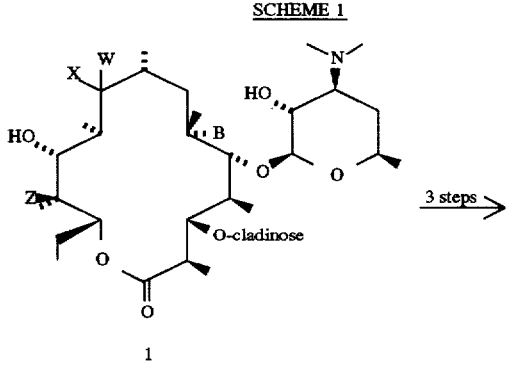

1

2

In accordance with Scheme 1 an erythromycin A (1,X+W=O, Z=OH, B=H or OMe) or erythromycin B (1, X+W=O, Z=H, B=H or OMe), or alternatively an oxime derivative of erythromycin A (1, X+W=NOR², as defined above, Z=OH, B=OH) or erythromycin B (1, X+W=NOR², Z=H, B=OH) compound (1) is converted into the desired 3-deoxy compound (2) by a series of reactions. The first removes the cladinose sugar moiety by reaction of the macrolide with a strong acid, for example 0.5–1.5N HCl or dichloroacetic acid, in a suspension in aqueous alcohol, such as for example, methanol, ethanol, or isopropanol, by stirring at ambient temperature for 0.5 to 24 hours, for example. After basification of the reaction mixture with a base such as an alkali metal base, the precipitated product is washed and dried. The 3-O-descladinose compound is then dissolved in an aprotic solvent such as THF, then reacted with an excess of NaH at from 0° to –30° C. under an inert atmosphere, followed by reaction of the intermediate anion with $CS_2$ and $CH_3I$ at –5 to 10° C., to form a 3-O-xanthyl compound. This xanthate intermediate is then reacted with 1.1–1.3 equivalents of $Bu_3SnH$ under an inert atmosphere in the presence of a catalytic amount of AIBN or other suitable radical initiator, in a solvent suitable for a free radical reaction, such as benzene or toluene, for example, at reflux conditions to afford the desired compound (2). In the case for (2) where B=OH and X+W=NOR, the 9-keto analog (X+W=O) can be prepared via known deoximation methods using, for example, $NaNO_2$ in the presence of aq. acid/MeOH, or using $NaHSO_3$/formic acid in $H_2O$/isopropanol at r.t to reflux, for example.

SCHEME 2

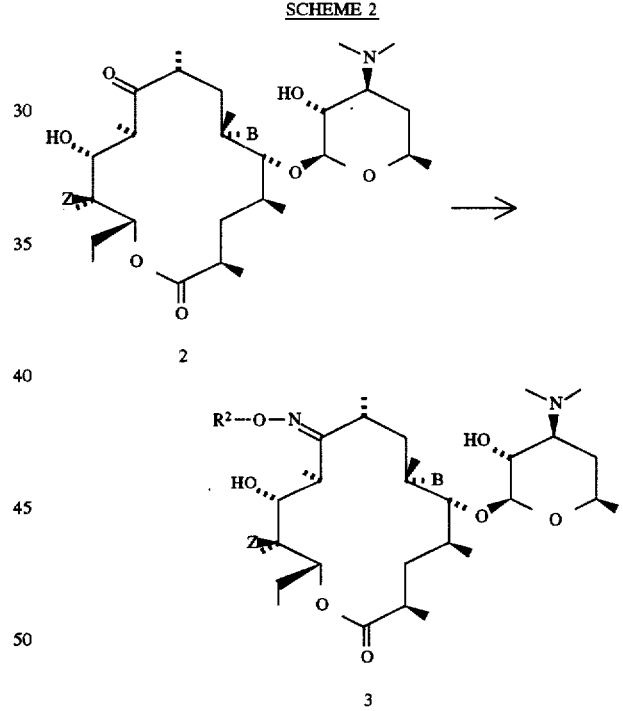

In accordance with Scheme 2 the compound (2) is reacted at its ketone group with an excess of hydroxylamine HCl in the presence of pyridine, or in an alcoholic solution in the presence of a base, such as an alkali metal base, pyridine or a trialkylamine, such as triethylamine, for example, at a temperature of from 50°–80° C. for 1–4 days, to give compound (3) wherein R² is hydrogen. In the event that compound (3) is desired to be a substituted oxime wherein R² represents $C_1$–$C_6$-alkyl, $C_1$–$C_6$-alkylamino, aryl-$C_1$–$C_6$-alkyl, or heteroaryl-$C_1$–$C_6$-alkyl, then compound (2) is reacted with an appropriately substituted hydroxylamine under the conditions described immediately above. Alternately, the compound (3) where R² is hydrogen may be reacted with an appropriate electrophile, such as an alkyl halide, for example, in an aprotic solvent in the presence of an appropriate base, to afford the substituted oxime (3), wherein $R^2$ is as described above.

temperatures for 8 to 48 hours, to prepare the intermediate 2'-protected macrolide (3A). Secondly, the 2'-protected intermediate is reacted with a suitable base, such as NaN

SCHEME 3

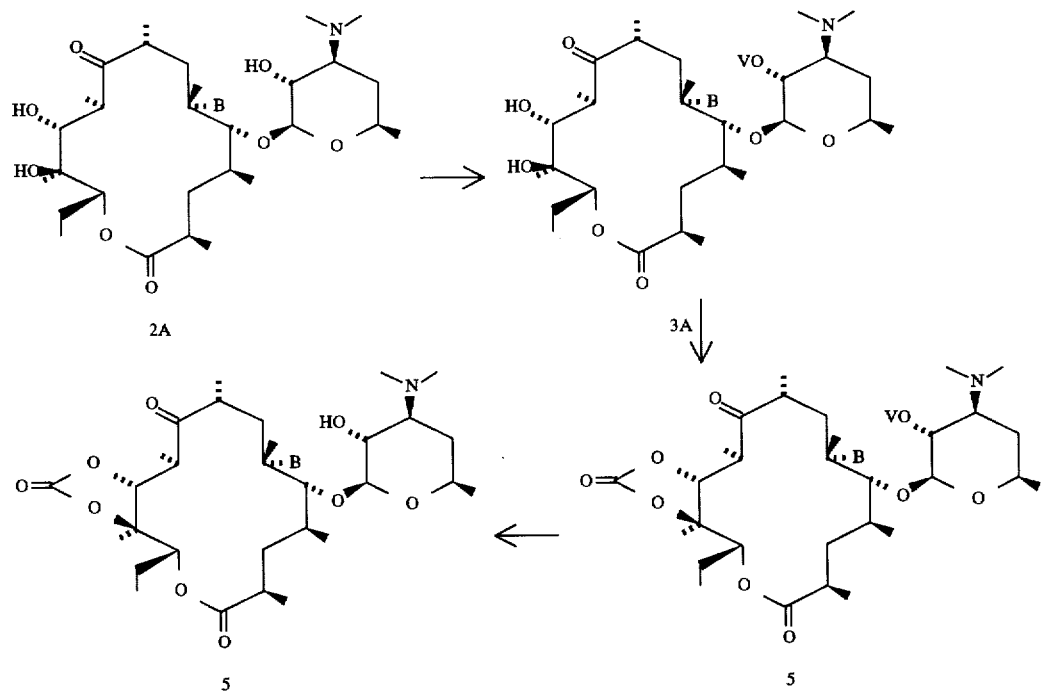

In accordance with Scheme 3, compounds of formula (2A) (i.e., of formula (2) wherein Z is hydroxyl) may be reacted in a stepwise manner to give the cyclic carbonate compound (5). First, compound (2A) is reacted with a hydroxy-reactive reagent, such as acetic anydride or benzoic anhydride in the presence of TEA or another base in a solvent such as methylene chloride at ambient or reflux $(TMS)_2$, in THF at $-40°$ C., followed by CDI in DMF at room temperature to prepare the 2'-protected-11,12-cyclic carbonate intermediate (4). Lastly, the 2'-protecting group is removed by stirring with methanol for 8–48 hours at ambient to reflux temperature to give the desired compound (5).

SCHEME 4

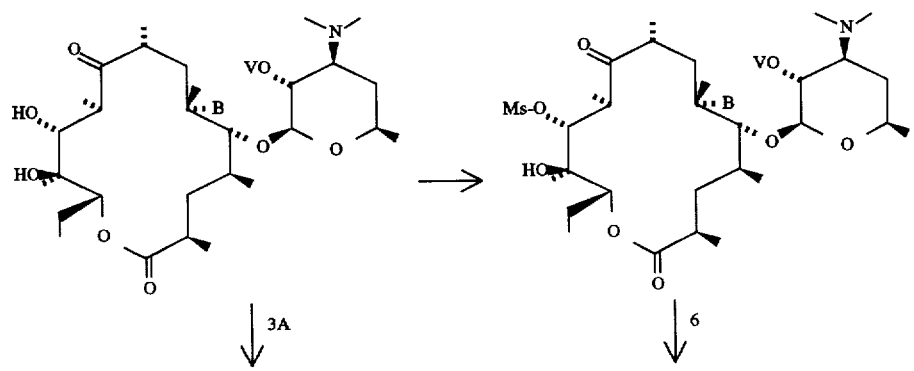

-continued
SCHEME 4

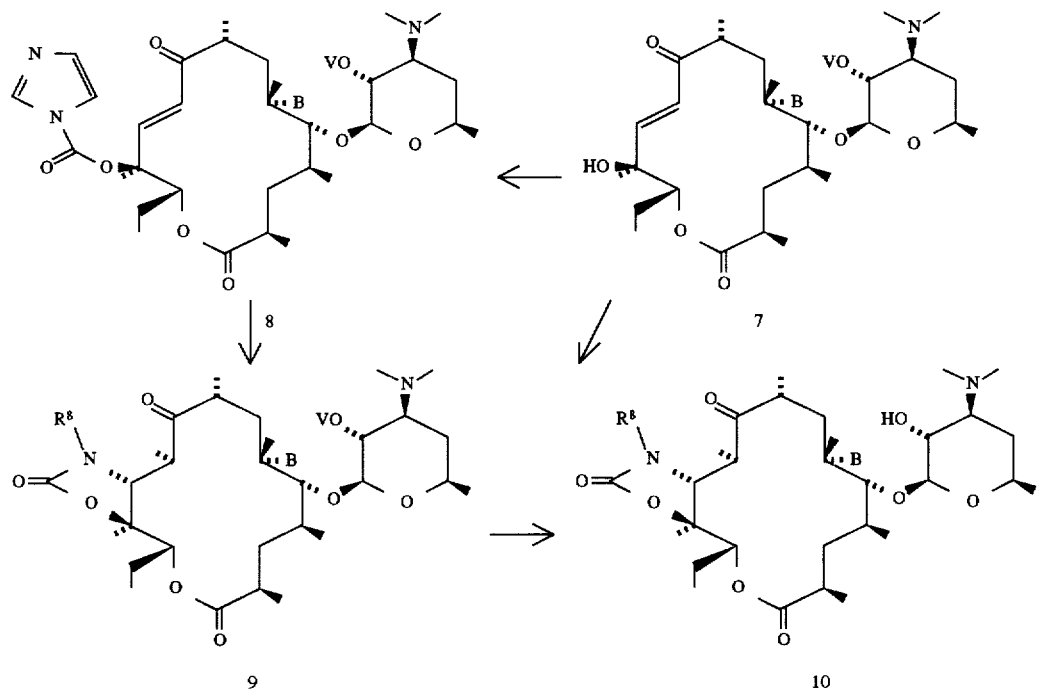

In accordance with Scheme 4 are prepared cyclic carbamate compounds of formula (10), i.e., compounds of Formula (III). First, the 2'-protected compound (3) is reacted with methanesulfonyl anhydride in pyridine at ambient temperature for 4–24 hours to prepare the 2'-protected-11-mesyl intermediate (6). Compound (6) is reacted with a base such as DBU in acetone at ambient temperature for 4–24 hours to give a 2'-protected-10,11-anhydro intermediate (7). Next the 2'-protected-10,11-anhydro intermediate is reacted with a base such as NaN(TMS)$_2$ in THF at −40° C., followed by CDI in DMF at room temperature to prepare a 12-acylimidazolide-10,11-anhydro intermediate (8). Compound (8) is reacted with an amine in a suitable solvent such as DMF or aqueous acetonitrile to give the 2'-protected compound (9). Lastly, the 2'-protecting group is removed by stirring with methanol for 8–48 hours at ambient temperature to give the desired compound (10). Alternately, compound (X) may be prepared directly from compound (3A) by a base such as NaN(TMS)$_2$ in THF at −40° C., followed by reaction with an excess of CDI. Also alternately, compound (7) can be directly converted to compound (9) by reaction with an alkyl, aryl, or alkaryl isocyanate, in some cases in the presence of a suitable catalyst such as CuBr, to yield directly the cyclic carbamate (9), wherein Y and Z are as defined above and $R^8$ is as defined above but additionally includes aryl and heteroaryl.

SCHEME 5

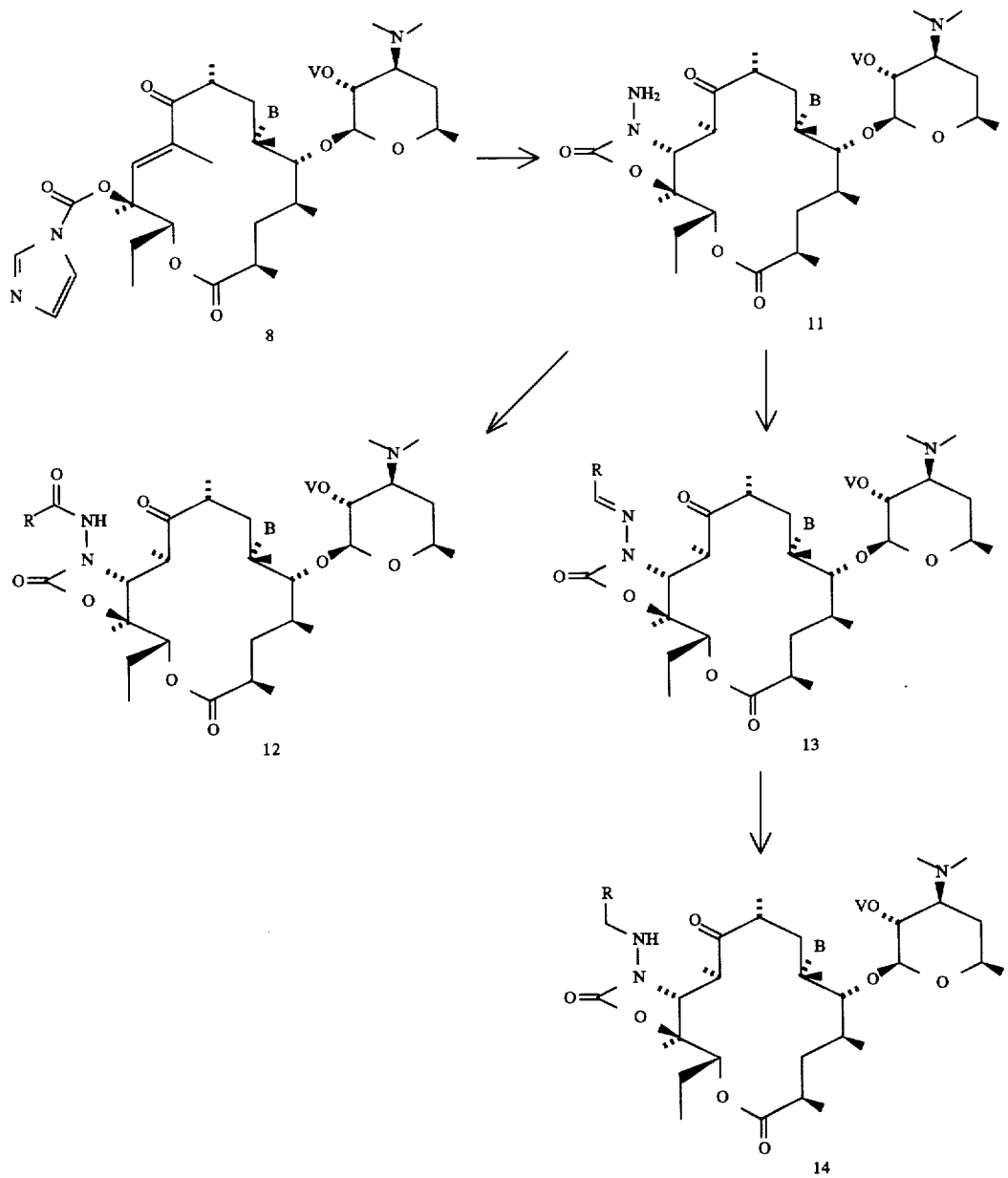

In accordance with Scheme 5 are prepared compounds of Formula (III) wherein $R^8$ is NH—$R^9$, wherein $R^9$ is as defined above. Compound 8 (prepared in Scheme 4) is reacted with an excess of hydrazine in an aprotic solvent, such as DMF or THF, at a temperature from ambient to reflux, for 4 to 24 hours, preferably in DMF at 60° C. for 6–10 hours to give compound (11). Compound (11) may then be treated with an acylating reagent, such as an acyl chloride or acyl anhydride, in an aprotic solvent or a carboxylic acid in the presence of EDCI-HCl, triethylamine and DMAP, for example, at ambient to reflux temperatures, for a period of 4–24 hours to give the acylated compound (12). Alternately, compound (11) may be treated with an aldehyde in an aprotic solvent, such as toluene, for example at reflux conditions to prepare the imine compound (13). The imine (13) may then be reduced with sodium cyanoborohydride, for example, in acetic acid and methanol for 6–24 hours to prepare the alkyl compound (14). Alternatively, the imine (13) may be reduced with hydrogen in the presence of a suitable catalyst, using $H_2$/10% Pd-C for example, in EtOAc or ethanol for 4–48 hours to prepare the alkyl compound (14).

EXAMPLES

The procedures described above for preparing the compounds of the present invention will be better understood in connection with the following examples, which are intended as an illustration of and not a limitation upon the scope of the invention. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

The NMR data for the central portion of the erythromycin compounds exemplified below are given in Table 1, which is placed after Example 8.

Example 1

Compound of Formula (I): A=H; B=methoxy; V= H; W and X taken together are =O; Y=Z=—OH 1a. 5-O-desosaminyl-6-O-methylerythronolide A A sample of clarithromycin (3-O-cladinosyl-5-O-desosaminyl-6-O-methylerythronolide A, Abbott Labs, 142.38 g, 190.35 mmol) was suspended in an ethanol-water (1700/600 mL) solution, and 341 mL of 1N HCl was added. The reaction mixture was stirred for 24 hours, and to this solution was then added 170 mL of 2M NaOH and an additional 250 mL of water with vigorous stirring. The precipitate was collected by filtration, washed with water and dried to afford the title compound (95.00 g, 84%). MS m/z: 590 (M+H)$^+$.

1b. Compound of Formula (I): A=O—(C=S)—S—CH$_3$; B=methoxy; V=H; W and X taken together are =O; Y=Z=—OH To a solution of 5-O-desosaminyl-6-O-methylerythronolide A (11.79 g, 20 mmoL, from step 1a above) in THF (100 mL) at −20° C. under an inert atmosphere was added NaH (1.80 g, 60 mmoL, 60% dispersion) slowly over a 5 minute period, and after several minutes CS$_2$ (1.2 mL, 20 mmoL) was added. After 5 minutes of additional stirring CH$_3$I (1.24 mL, 20 mmol) was added, and the reaction mixture was allowed to gradually warm to −5°–0° C. After 1 hour the reaction mixture was diluted with EtOAc (400 mL), then washed with 100 mL portions of saturated aqueous NaHCO$_3$ (1x) and brine (1x), dried (MgSO$_4$), and concentrated to afford the crude product as a yellowish foam. Chromatographic purification (silica, CHCl$_3$; CHCl$_3$—MeOH (95:5) followed by addition of hexane, filtration, and concentration, afforded the title compound as a white foam (7.68 g; 56%). MS m/z: 680 (M+H)$^+$. Anal. Calc'd. for C$_{32}$H$_{57}$NO$_{10}$S$_2$: C, 56.52; H, 8.45; N, 2.06; Found: C, 56.95; H, 8.65; N, 1.92.

1c. Compound of Formula (I): A=H; B=methoxy; V=H; W and X taken together are =O; Y=Z=—OH A solution of the compound from step 1b (20.00 g; 29.41 mmoL), Bu$_3$SnH (9.49 mL, 35.29 mmol) and AIBN (~50 mg, catalytic) in benzene (200 mL) was refluxed (adding 25 mg portions of AIBN periodically) for 8 hours, then the organic layer washed with 100-mL portions of 10% aq KF (1x) and brine (1x), dried (MgSO$_4$), and concentrated to afford the crude product as an oil. Chromatographic purification (silica, CHCl$_3$; CHCl$_3$—MeOH (97.5:2.5) followed by recrystallization from hexane afforded the title compound as a white crystalline material (5.48 g; 32%). MS m/z: 574 (M+H)$^+$. Anal. Calc'd. for C$_{30}$H$_{55}$NO$_9$: C, 62.80; H, 9.66; N, 2.44; Found: C, 63.02; H, 9.74; N, 2.30.

Example 2

Compound of Formula (I): A=H; B=methoxy; V= H; W and X taken together are =N—OH; Y=Z=—OH;

A sample of the compound of Example 1 (150 mg, 0.26 mmol) and hydroxylamine HCl (72 mg, 1.03 mL, Aldrich) were dissolved in 2 mL of pyridine, and the mixture was heated at 70° C. for 24 hours. Additional hydroxylamine HCl (72 mg) was added, and the heating was continued as before for another 24 hours. The solvent was removed under vacuum, and the residue was dissolved in methylene chloride. This solution was washed with saturated aqueous NaHCO$_3$ solution and brine, dried over MgSO$_4$ and concentrated to give 112 mg of crude product. The residue was purified by flash chromatography on silica gel, eluting with 3–10% methanol in chloroform to afford the title compound (19 mg). MS m/z: 589 (M+H)$^+$. High resolution MS: calcd. for C$_{30}$H$_{57}$N$_2$O$_9$: 589.4064; Found: 589.4046. $^{13}$C NMR and 1H NMR data are given in Table 1 below.

Example 3

Compound of Formula (II): A=H; B=methoxy; V= H; W and X taken together are =O

3a. Compound of Formula (I): A=H; B=methoxy; V=acetyl; W and X taken together are =O; Y=Z=—OH;

A sample of the compound of Example 1 (573 mg, 1.0 mmol), 0.188 mL of acetic anhydride and 0.278 mL of TEA were dissolved in 10 mL of methylene chloride, and the reaction mixture was stirred at room temperature for 20 hours. The reaction mixture was diluted with 40 mL of methylene chloride, and the organic solution was washed with satd. aqueous NaHCO$_3$ and brine, then dried and concentrated to obtain the title compound (600 mg). MS m/z: 616 (M+H)$^+$.

3b. Compound of Formula (II): A=H; B=methoxy; V=acetyl; W and X taken together are =O Under Argon a 150 mg (0.243 mmol) sample of the compound from step 3a was dissolved in THF and cooled to −35° C. NaN(TMS)$_2$ (0.268 mL, 0.268 mmol, Aldrich, 1.0M in THF) was added, the reaction mixture was stirred for ten minutes, and a solution of CDI (142 mg, 0.877 mmol, Aldrich) in 2.5 mL of THF was added. The cooling bath was removed, and 15 minutes later the reaction was quenched by the addition of 35 mL of ethyl acetate and 15 mL of satd. aqueous NaHCO$_3$. The organic layer was separated, washed with brine, dried and concentrated to yield the title compound (174 mg). MS m/z: 642 (M+H)$^+$.

3c. Compound of Formula (II): A=H; B=methoxy; V=H; W and X taken together are =O A 164 mg sample of the compound from step 3b was dissolved in methanol and stirred for 19 hours at room temperature. The solvent was removed under vacuum, and the residue was flash chromatographed on silica gel, eluting with 2.5% methanol in chloroform to afford the title compound (54 mg). MS m/z: 589 (M+H)$^+$. Anal. Calc'd. for C$_{31}$H$_{53}$NO$_{10}$: C, 62.08; H, 8.91; N, 2.33; Found: C, 61.80; H, 9.14; N, 2.20.

Example 4

Compound of Formula (III): A=H; B=methoxy; V= H; W and X taken together are =O; R$^{10}$=—CH$_2$—CH$_2$—CH$_2$—CH$_2$-phenyl 4a. Compound of (8) from Scheme 4: B=methoxy; V=acetyl A sample of the compound from Example 3a above (0.63 g, 1.023 mmol) was dissolved in 10 mL of THF, and the solution was cooled to −60° C. To this stirred solution was added 1.22 mL of sodium bis(trimethyldisilyl) amide (1.0M in THF). After 4 hours 1,1-carbonyldiimidazole (0.66 g, 4.09 mmol) was added as a solution in 6 mL of 2:3 DMF/THF, and the reaction mixture was slowly warmed to room temperature and stirred for 16 hours. The reaction was quenched by addition of 5% aqueous NaH$_2$PO$_4$, and the resulting mixture was extracted with chloroform. The organic layer was washed with water, dried over MgSO$_4$ and concentrated to give the title compound. MS m/z: 692 (M+H)$^+$.

4b. Compound of Formula (III): A=H; B=methoxy; V=acetyl; W and X taken together are =O; $R^{10}$=—$CH_2$—$CH_2$—$CH_2$—$CH_2$-phenyl A sample of the compound from step 4a (0.1 g, 0.144 mmol) was dissolved in 10% aqueous acetonitrile, 4-phenylbutylamine (0.11 mL, 0.722 mmol) was added, and the reaction mixture was stirred for 16 hours. The solution was diluted with methylene chloride, and the organic layer was separated and washed (3x) with 5% aqueous $NaH_2PO_4$. The organic layer was dried ever $Na_2SO_4$ and concentrated, and the residue was purified by flash chromatography on silica gel, eluting with 2–5% ethanol in chloroform to afford 65 mg (59%) of the title compound. MS m/z: 773 $(M+H)^+$.

4c. Compound of Formula (III): A=H; B=methoxy; V=H; W and X taken together are =O; $R^{10}$=—$CH_2$—$CH_2$—$CH_2$—$CH_2$-phenyl A 65 mg sample of the compound from step 4b was dissolved in methanol and stirred at room temperature for 16 hours. The title compound was obtained (45 mg) after filtration and removal of the solvent. MS m/z: 731 $(M+H)^+$. High resolution MS: calculated for $C_{41}H_{66}N_2O_9$: 730.985; found, 730.772. Anal. Calc'd. for $C_{41}H_{66}N_2O_9$: C, 67.36; H, 9.10; N, 3.83; Found: C, 67.53; H, 9.17; N, 3.94.

Example 5

Compound of Formula (III): A=H; B=methoxy; V=H; W and X taken together are =O; $R_{10}$=—$CH_2$—$CH_2$-phenyl-4-O-phenyl 5a. Compound of Formula (III): A=H; B=methoxy; V=acetyl; W and X taken together are =O; $R^{10}$=—$CH_2$—$CH_2$-phenyl-4-O-phenyl A sample of the compound from step 4a (0.18 g, 0.26 mmol) was dissolved in 10% aqueous acetonitrile, 4-phenoxyphenethylamine (0.28 g, 1.3 mmol, Trans World Chemical) was added, and the reaction mixture was stirred for 16 hours. The solution was diluted with methylene chloride, and the mixture was washed (3x) with saturated aqueous $NaH_2PO_4$. The organic layer was dried over $Na_2SO_4$ and concentrated, and the residue was purified by flash chromatography on silica gel, eluting with 1–5% ethanol in chloroform to yield 80 mg (36%) of the title compound. MS m/z: 837 $(M+H)^+$.

5b. Compound of Formula (III): A=H; B=methoxy; V=H; W and X taken together are =O; $R^{10}$=—$CH_2$—$CH_2$-phenyl-4-O-phenyl A 50 mg sample of the compound from step 5a was dissolved in methanol and stirred at room temperature for 16 hours. The desired compound was obtained (40 mg) after filtration and removal of the solvent. MS n/z: 795 $(M+H)^+$. Anal. Calc'd. for $C_{45}H_{66}N_2O_{10}$: C, 67.98; H, 8.36; N, 3.52; Found: C, 67.74; H, 8.46; N, 3.59. The $R^8$ $^{13}$C-NMR peaks are: 157.6, 45.3, 32.1,157.2, 155.3, 133.8,130.1, 129.5, 122.8, 119.0, 118.5, and the 1H-NMR peaks are: 3.85, 3.79, 2.98, 2.90, 7.49 to 6.79.

Example 6

Compound of Formula (I): A=H; B=methoxy; V=H; W and X taken together are =N—O—$CH_3$; Y=Z=—OH A sample of the compound from Example 1 (100 mg, 0.174 mmol), methoxylamine HCl (140 mg, 1.74 mmol) and $CaCO_3$ (110 mg, 1.04 mmol) were suspended in 5 mL of methanol, and the reaction mixture was refluxed under an inert atmosphere for 16 hours. The solvent was removed under vacuum, and the residue was triturated with ethyl acetate. The solvent was filtered, washed with saturated $NaHCO_3$ and brine, dried over $Na_2SO_4$ and concentrated. The residue was purified by flash chromatography on silica gel, eluting with chloroform containing 0.5% TEA to give the title compound. MS m/z: 603 $(M+H)^+$. The $R^8$ $^{13}$C-NMR peaks are: 157.6, 43.4, 27.1, 28.6, 35.6, 128.4 to 125.6, and the $^1$H-NMR peaks are: : 3.67, 3.59, 1.69, 1.65, 2.67, 7.36–7.04.

Example 7

Compound of Formula (I): A=H; B=methoxy; V=H; W and X taken together are =N—O—$CH_2$—$CH_3$; Y=Z=—OH To a sample of the compound from Example 1 (200 mg, 0.348 mmol) dissolved in 2.5 mL of methanol were added ethoxylamine HCl (340 mg, 3.48 mmol) and TEA (0.3 mL, 2.09 mmol), and the reaction mixture was stirred for 16 hours at reflux temperature. The reaction mixture was diluted with chloroform, and the solution was washed with $NaHCO_3$ and brine, dried over $Na_2SO_4$ and concentrated. The residue was purified by flash chromatography on silica gel, eluting with 1 % methanol in chloroform containing 0.5%–1% TEA to give the title compound. MS m/z: 617 $(M+H)^+$. Anal. Calc'd. for $C_{32}H_{60}N_2O_9$: C, 62.31; H, 9.80; N, 4.54; Found: C, 62.60; H, 9.90; N, 4.89.

Example 8

Compound of Formula (I): A=H; B=methoxy; V=H; W and X taken together are =N—O—$CH_2$—O—$CH_2$—$CH_2$—O—$CH_3$; Y=Z=—OH A sample of the compound from Example 2 (100 mg, 0.17 mmol), $Na_2CO_3$ (90 mg, 0.85 mmol) and 2-methoxyethyoxymethyl chloride (0.02 mL, 0.22 mmol) were suspended in 5 mL of acetone and the reaction mixture was stirred for 16 hours at reflux temperature, after which an additional 0.1 mL of 2-methoxyethyoxymethyl chloride was added. The solvent was removed under vacuum, and the residue was triturated with ethyl acetate. The solvent was filtered, washed with saturated aqueous $NaHCO_3$ and brine, dried over $Na_2SO_4$ and concentrated. The residue was purified by flash chromatography on silica gel, eluting with chloroform containing 0.5% TEA to give the title compound. MS m/z 677 (M+1).

TABLE 1

| | | | | | | | | | | | | | | | | |
|---|---|---|---|---|---|---|---|---|---|---|---|---|---|---|---|---|
| | | | | | | | | Chemical Shift | | | | | | | | |
| Erythronolide | | 3-desclad-Clarithromycin | | Example 1 | | Example 2 | | Example 3 | | Example 4 | | Example 5 | | Example 6 | | Example 7 |
| Atom Number | 13C NMR | 13C NMR | 1H-NMR | 13C NMR | 1H-NMR | 13C NMR | 1H-NMR | 13C NMR | 1H-NMR | 13C NMR | 1H-NMR | 13C NMR | 1H-NMR | 13C NMR | 1H-NMR | 13C NMR | 1H-NMR |
| 1 | 175 | | | 176.8 | | 176.8 | | 177 | | 177.1 | | 177.2 | | 176.8 | | 176.8 | |
| 2 | 44.6 | 2.65 | | 38.4 | 2.62 | 38.5 | 2.63 | 38.8 | 2.66 | 38.4 | 2.72 | 38.4 | 2.69 | 38.4 | 2.64 | 38.5 | 2.61 |
| 2-Me | 15.2 | 1.25 | | 17.8* | 1.11 | 18.9 | 1.14 | 18.9 | 1.17 | 18.7 | 1.19 | 18.7 | 1.16 | 18.8 | 1.14 | 18.9 | 1.11 |
| 3 | 79 | 3.56 | | 46.3 | 1.64–1.41 | 46.2 | 1.67–1.40 | 46.2 | 1.70–1.50 | 45.8 | 1.65–1.52 | 45.8 | 1.64–1.49 | 46.1 | 1.66–1.40 | 46.1 | –1.64–1.38 |
| 4 | 35.9 | 2.11 | | 30.9 | 1.84 | 31 | 1.9 | 31.2 | 1.74 | 31 | 1.85 | 30.9 | 1.86 | 30.9 | 1.88 | 31 | 1.87 |
| 4-Me | 8.2 | 1.12 | | 15.2 | 1.14 | 15.2 | 1.12 | 15.4 | 1.15 | 15.1 | 1.17 | 15.1 | 1.15 | 15.3 | 1.11 | 15.4 | 1.08 |
| 5 | 88.5 | 3.68 | | 84 | 3.54 | 83.5 | 3.56 | 84 | 3.57 | 83.8 | 3.58 | 83.5 | 3.57 | 83.4 | 3.54 | 83.5 | 3.53 |
| 6 | 78.1 | | | 77.9 | | 78.3 | | 78.1 | | 78.5 | | 78.4 | | 78.2 | | 78.3 | |
| 6-Me | 18.8 | 1.36 | | 18.9* | 1.25 | 19.3 | 1.34 | 49.3 | 2.96 | 19.4 | 1.29 | 19.4 | 1.3 | 19.2 | 1.31 | 19.2 | 1.28 |
| O-Me | 49.5 | 2.96 | | 49.5 | 2.95 | 49.9 | 3.02 | 19.3 | 1.29 | 49.4 | 2.94 | 49.7 | 3.02 | 49.5 | 3 | 49.6 | 2.96 |
| 7 | '38.8 | 1.92–1.55 | | 39 | 1.90–1.52 | 37.5 | 1.60–1.37 | 39 | 1.80–1.58 | 38.8 | 1.83–1.58 | 38.8 | 1.83–1.58 | 37.5 | 1.58–1.35 | 37.5 | 1.55–1.32 |
| 8 | 45.5 | 2.57 | | 45.6 | 2.53 | 25.4 | 3.77 | 45.2 | 2.62 | 45.6 | 2.58 | 45.7 | 2.59 | 26.2 | 3.64 | 26.2 | 3.65 |
| 8-Me | 17.7 | 1.12 | | 19.2* | 1.08 | 18.4 | 0.99 | 18.2 | 1.1 | 18.6 | 1.12 | 18.6 | 1.12 | 18.3 | 0.95 | 18.4 | 0.93 |
| 9 | 220.6 | | | 220.8 | | 171.2 | | 212 | | 215.7 | | 215.8 | | 170 | | 169.5 | |
| 10 | 37.5 | 3.01 | | 37.4 | 2.98 | 33.1 | 2.61 | 37.6 | 2.96 | 39.i | 3.08 | 39 | 3.11 | 32.8 | 2.56 | 32.8 | 2.54 |
| 10-Me | 12.6 | 1.12 | | 12.7 | 1 | 15.2 | 1.16 | 12.9 | 1.19 | 14.2 | 1.06 | 14.3 | 1.05 | 15.1 | 1.16 | 15.1 | 1.13 |
| 11 | 69.8 | 3.85 | | 69.6 | 3.93 (OH3.91) | 70.6 | 3.95 | 81.1 | 4.85 | 60.8 | 3.78 | 60.9 | 3.83 | 70.6 | 3.93 | 70.6 | 3.9 |
| 12 | 74.2 | | | 74.2 | (OH 3.22) | 74.2 | | 85 | | 82.9 | | 83 | | 74 | | 74 | |
| 12-Me | 16.2 | 1.18 | | 16.2* | 1.11 | 16.3 | 1.19 | 13.1 | 1.51 | 14.3 | 1.45 | 14.2 | 1.44 | 16.2 | 1.18 | 16.2 | 1.16 |
| 13 | 76.6 | 5.17 | | 76.6 | 5.15 | 76.9 | 5.24 | 75.2 | 5.14 | 76.2 | 5.11 | 76 | 5.08 | 76.9 | 5.22 | 76.9 | 5.2 |
| 14 | 21.4 | 1.95–1.48 | | 21.5 | 1.90–1.45 | 21.7 | 1.96–1.49 | 22.3 | 1.90–1.56 | 22.4 | 1.94–1.52 | 22.3 | 1.91–1.51 | 21.6 | 1.96–1.48 | 21.7 | 1.94–1.45 |
| 15 | 10.4 | 0.83 | | 10.5 | 0.81 | 10.6 | 0.85 | 10.2 | 0.88 | 10.3 | 0.85 | 10.1 | 0.82 | 10.5 | 0.84 | 10.6 | 0.82 |
| | | | | | | | | | | 104.4 | 4.21 | 104.2 | 4.18 | 104.1 | 4.16 | 104.2 | 4.13 |

Example 9

Compound of Formula (III): A=H; B=methoxy; V=H; W and X taken together are =O; $R^{10}$=$NH_2$ Hydrazine is added to a solution of the compound from step a of Example 4 in DMF, and the reaction mixture stirred at room temperature. Upon completion of the reaction the mixture is partitioned between EtOAc and $H_2O$, the layers separated, and the aqueous portion extracted with additional portions of EtOAc. The combined organic layers are then washed with $H_2O$ and brine, dried ($Na_2SO_4$), and concentrated under reduced pressure. Purification by flash chromatography affords the desired 2'-protected compound. This material is dissolved in MeOH and stirred at room temperature overnight, then the reaction mixture is concentrated under reduced pressure and purified by flash chromatography to give the title compound.

Example 10

Compound of Formula (I): A=H; B=hydroxy; V=H; W and X taken together are =O; Y=Z=—OH 10a. 5-O-desosaminyl-9-benzyloximo Erythronolide A A solution of 5-O-desosaminyl erythronolide A oxime (prepared according to the procedure of LeMahieu, et al., *J. Med. Chem.*, 17:953–956, (1974)) in THF is treated with NaH followed by benzyl bromide at 0° C. under an inert atmosphere, and the reaction mixture is allowed to gradually warm to room temperature. After several hours the reaction mixture is quenched into EtOAc. The organic layer is washed with saturated aqueous $NaHCO_3$ and brine, dried ($MgSO_4$), and concentrated to afford the crude product. Chromatographic purification (silica, $CHCl_3$; $CHCl_3$—MeOH (95:5) affords the title compound.

10b. Compound of Formula (I): A=O—(C=S)—S—$CH_3$; B=hydroxy; V=H; W and X taken together are =N—O—benzyl; Y=Z=—OH To a solution of the compound from step 10a in THF at −20° C. under an inert atmosphere is added NaH (excess) slowly over a 5 minute period, and after several minutes $CS_2$ is added. Several minutes later MeI is added, and the reaction mixture allowed to gradually warm to 10° C. After 1 hour the reaction mixture is quenched into EtOAc. The organic layer is washed with saturated aqueous $NaHCO_3$ and brine, dried ($MgSO_4$), and concentrated to afford the crude product. Chromatographic purification (silica, $CHCl_3$; $CHCl_3$—MeOH affords the title compound.

10c. Compound of Formula (I): A=O—(C=S)—S—$CH_3$; B=hydroxy; V=H; W and X taken together are =N—O—benzyl; Y=Z=—OH A solution of the compound from step 10b, $Bu_3SnH$ (1.2 eq) and AIBN (catalytic) in benzene is refluxed (adding 25 mg portions of AIBN periodically) for 8 hours, then the organic layer washed with brine (1x), dried ($MgSO_4$), and concentrated to afford the crude product. Chromatographic purification (silica, $CHCl_3$; $CHCl_3$—MeOH) affords the title compound.

10d. Compound of Formula (I): A=H; B=hydroxy; V=H; W and X taken together are =O; Y=Z=—OH A solution of the compound from step 10c in EtOH is hydrogenated using 10% Pd-C under one atmosphere hydrogen, and upon completion of the reaction the mixture is filtered through celite to give the free oxime. De-oximation according to the procedure of LeMahieu, et al. (op. cit.) followed by chromatographic purification (silica, $CHCl_3$; $CHCl_3$—MeOH) affords the title compound.

Example 11

Compound of Formula (III): A=H; B=methoxy; V=H; W and X taken together are =O; R$^8$=—NH—CO—CH$_3$ 11a. Compound (10) Scheme 4: B=methoxy; V=hydrogen; R$^8$=—NH$_2$ Hydrazine is added to a solution of the compound from Example 4 step a in DMF, and the reaction mixture is stirred at room temperature. Upon completion of the reaction the mixture is partitioned between EtOAc and H$_2$O, the layers are separated, and the aqueous portion is extracted with additional portions of EtOAc. The combined organic layers are then washed with H$_2$O and brine, dried (Na$_2$SO$_4$), and concentrated under reduced pressure. Purification by flash chromatography affords the 2'-acetyl-protected compound. This material is dissolved in MeOH and stirred at room temperature overnight, then the reaction mixture is concentrated under reduced pressure and purified by flash chromatography to give the title compound.

11b. Compound of Formula (III): A=H; B=methoxy; V=H; W and X taken together are =O; R$^8$=—NH—CO—CH$_3$ A sample of the compound from step 11a is dissolved in CH$_2$Cl$_2$ and treated with acetic anhydride and 4-dimethylaminopyridine. After stirring under nitrogen for 1X hours, the reaction is quenched by addition of saturated NaHCO$_3$ solution and extracted into CH$_2$Cl$_2$. The organic portion is washed with H$_2$O and brine, dried (Na$_2$SO$_4$), and concentrated under reduced pressure. Purification by flash chromatography gives the 2'-acetyl-protected compound. This material is dissolved in MeOH and stirred at room temperature overnight, then the reaction mixture is concentrated under reduced pressure and purified by flash chromatography to give the title compound.

Example 12

Compound of Formula (III): A=H; B=methoxy; V=H; W and X taken together are =O; R$^8$=—N=CH-phenyl To a sample of the compound from step 11a dissolved in toluene is added benzaldehyde and a small amount of powdered 4 Å molecular sieves. The mixture is heated to near reflux under nitrogen for 16 hours, then the reaction mixture is cooled, filtered, and concentrated under reduced pressure. The residue is purified by flash chromatography eluting with MeOH/CH$_2$Cl$_2$ to give the title compound.

Example 13

Compound of Formula (III): A=H; B=methoxy; V=H; W and X taken together are =O; R$^8$=—NH$_2$—CH$_2$-phenyl The compound from Example 12 is dissolved in MeOH and 10% Pd on carbon is added. The reaction is then stirred vigorously under 1 atm of H$_2$ pressure for several days, then the reaction mixture is filtered and concentrated under reduced pressure. Purification of the residue by flash chromatography gives the title compound.

Example 14

Compound of Formula (III): A=H; B=methoxy; V=H; W and X taken together are =O; R$^8$=—CH$_2$—CH$_2$—CH$_2$-phenyl Following the procedure of Example 12, replacing the benzaldehyde thereof with 3-phenylpropanal, the corresponding imine is prepared. This imine compound is dissolved in CH$_3$CN and reacted with NaCNBH$_3$ (excess). Acetic acid is added to adjust the pH to 4–6. The reaction is then stirred under nitrogen for 1 day, the reaction is quenched by addition of saturated NaHCO$_3$ solution, and the product is extracted into CH$_2$Cl$_2$. The organic portion is washed with H$_2$O and brine, dried (Na$_2$SO$_4$) and concentrated under reduced pressure. Purification by flash chromatography gives the title compound.

Examples 15A–15f

Following the procedures of Example 11, except substituting the starting material shown below for the acetic anhydride of Example 11, the title compounds of Examples 15a–15f are prepared as indicated in Table 2 below.

TABLE 2

| Ex. No | Starting Material | Title Compound |
|---|---|---|
| 15a | Benzoyl chloride | Compound of Formula III: A = H; B = methoxy; V = H; W and X taken together are O; R$^8$ = NH—CO—C$_6$H$_5$ |
| 15b | Phenylacetyl chloride | Compound of Formula III: A = H; B = methoxy; V = H; W and X taken together are O; R$^8$ = NH—CO—CH2—C$_6$H$_5$ |
| 15c | Phenylpropionyl chloride | Compound of Formula III: A = H; B = methoxy; V = H; W and X taken together are O; R$^8$ = NH—CO—CH2CH2C$_6$H$_5$ |
| 15d | Cinnamoyl chloride | Compound of Formula III: A = H; B = methoxy; V = H; W and X taken together are O; R$^8$ = NH—CO—CH$_2$—CH$_2$—C$_6$H$_5$ |
| 15e | Methylmalonyl chloride | Compound of Formula III: A = H; B = methoxy; V = H; W and X taken together are O; R$^8$ = NH—CO—CH$_2$—COOMe |
| 15f | 3-(4-quinoyl)-propionyl chloride | Compound of Formula III: A = H; B = methoxy; V = H; W and X taken together are O; R$^8$ = NH—CO—CH$_2$—CH$_2$-4-quinoyl) |

Examples 16a–16xx

Following the procedures of Example 12, except substituting the starting material shown below for the benzaldehyde of Example 12, the title compounds of Examples 16a–16g are prepared as indicated in Table 3 below.

TABLE 3

| Ex. No | Starting Material | Title Compound |
|---|---|---|
| 16a | acetaldehyde | Compound of Formula III: A = H; B = methoxy; V = H; W and X taken together are O; R$^8$ = N=CH—CH$_3$ |
| 16b | phenylacetaldehyde | Compound of Formula III: A = H; B = methoxy; V = H; W and X taken together are O; R$^8$ = N=CH—CH$_2$C$_6$H$_5$ |
| 16c | phenylpropionaldehyde | Compound of Formula III: A = H; B = methoxy; V = H; W and X taken together are O; R$^8$ = N=CH—CH$_2$CH$_2$C$_6$H$_5$ |
| 16d | cinnamylaldehyde | Compound of Formula III: A = H; B = methoxy; V = H; W and X taken together are O; R$^8$ = N=CH—CH=CH-phenyl |
| 16e | 3-(4-quinoyl)-propionaldehyde | Compound of Formula III: A = H; B = methoxy; V = H; W and X taken |

TABLE 3-continued

| Ex. No | Starting Material | Title Compound |
|---|---|---|
| | | together are O; R⁸ = N=CH—CH₂—CH₂—(4-quinoyl) |
| 16f | cyclopentanecarboxaldehyde | Compound of Formula III: A = H; B = methoxy; V = H; W and X taken together are O; R⁸ = N=CH-cyclopentane |
| 16f | 2-cyclohexylethanal | Compound of Formula III: A = H; B = methoxy; V = H; W and X taken together are O; R⁸ = N=CH—CH₂-cyclohexane |

Examples 17a–17

Following the procedures of Example 14, except substituting the starting material shown below for the 3-phenylpropanal of Example 14, the title compounds of Examples 17a–17xx are prepared as indicated in Table 4 below.

TABLE 4

| Ex. No | Starting Material | Title Compound |
|---|---|---|
| 17a | acetaldehyde | Compound of Formula III: A = H; B = methoxy; V = H; W and X taken together are O; R⁸ = NH-ethyl |
| 17b | benzaldehyde | Compound of Formula III: A = H; B = methoxy; V = H; W and X taken together are O; R⁸ = NH—CH₂C₆H₅ |
| 17c | phenylacetaldehyde | Compound of Formula III: A = H; B = methoxy; V = H; W and X taken together are O; R⁸ = NH— |
| 17d | phenylpropionaldehyde | Compound of Formula III: A = H; B = methoxy; V = H; W and X taken together are O; R⁸ = NH—CH₂—CH₂—CH₂—C₆H₅ |
| 17e | cinnamylaldehyde | Compound of Formula III: A = H; B = methoxy; V = H; W and X taken together are O; R⁸ = NH—CH₂—CH=CH-phenyl |
| 17f | 3-(4-quinoyl)-propionaldehyde | Compound of Formula III: A = H; B = methoxy; V = H; W and X taken together are O; R⁸ = NH—CH₂—CH₂—CH₂-(4-quinoyl) |
| 17g | 2-cyclohexylethanal | Compound of Formula III: A = H; B = methoxy; V = H; W and X taken together are O; R⁸ = NH—CH—CH₂-cyclohexane |

Examples 18a–18h

Following the procedures of Example 4, except substituting the starting material shown below for the starting material of Example 4, the title compounds of Examples 18a–18h are prepared as indicated in Table 5 below.

TABLE 5

| Ex. No | Starting Material | Title Compound |
|---|---|---|
| 18a | ammonia | Compound of Formula III: A = H; B = methoxy; V = H; W and X taken together are O; R⁸ = H |
| 18b | methylamine | Compound of Formula III: A = H; B = methoxy; V = H; W and X taken together are O; R⁸ = Me |
| 18c | benzylamine | Compound of Formula III: A = H; B = methoxy; V = H; W and X taken together are O; R⁸ = benzyl |
| 18d | phenylethylamine | Compound of Formula III: A = H; B = methoxy; V = H; W and X taken together are O; R⁸ = phenylethyl |
| 18e | phenylpropylamine | Compound of Formula III: A = H; B = methoxy; V = H; W and X taken together are O; R⁸ = phenylpropyl |
| 18f | 4-(4-quinoyl)butylamine | Compound of Formula III: A = H; B = methoxy; V = H; W and X taken together are O; R⁸ = —CH₂—CH₂—CH₂—CH₂-(4-quinoyl) |
| 18g | cyclohexylamine | Compound of Formula III: A = H; B = methoxy; V = H; W and X taken together are O; R⁸ = cyclohexyl |
| 18h | 2-cyclohexylethaneamine | Compound of Formula III: A = H; B = methoxy; V = H; W and X taken together are O; R⁸ = —CH₂—CH₂-cyclohexyl |

Example 19

Compound of Formula (III): A=H; B=methoxy; V=H; W and X taken together are =O; R⁸=phenyl A solution of compound 7 of scheme 4 (B=OMe; V=OAc) in THF is treated with NaH followed by phenylisocyanate and a catalytic amount of Cu(I)Br. After refluxing under nitrogen for 6–24 hours, the reaction is quenched by addition of satd. NaHCO₃ solution and extracted into CH₂Cl₂. The organic portion is washed with H₂O and brine, dried (Na₂SO₄), and concentrated under reduced pressure. Purification by flash chromatography gives the product as the 2'-O-acetate. This material is dissolved in MeOH and stirred at r.t. overnight, then the reaction mixture is concentrated under reduced pressure and purified by flash chromatography to give the title compound as a solid.

Example 19

In Vitro Assay of Antibacterial Activity

Representative compounds of the present invention were assayed in vitro for antibacterial activity as follows: Twelve petri dishes containing successive aqueous dilutions of the test compound mixed with 10 mL of sterilized Brain Heart Infusion (BHI) agar (Difco 0418-01-5) were prepared. Each plate was inoculated with 1:100 (or 1:10 for slow-growing strains, such as Micrococcus and Streptococcus) dilutions of up to 32 different microorganisms, using a Steers replicator block. The inoculated plates were incubated at 35°–37° C. for 20 to 24 hours. In addition, a control plate, using BHI agar containing no test compound, was prepared and incubated at the beginning and end of each test.

An additional plate containing a compound having known susceptibility patterns for the organisms being tested and belonging to the same antibiotic class as the test compound was also prepared and incubated as a further control, as well as to provide test-to-test comparability. Erythromycin A was used for this purpose.

After incubation, each plate was examined. The minimum inhibitory concentration (MIC) was defined as the lowest concentration of drug yielding no growth, a slight haze, or sparsely isolated colonies on the inoculum spot as compared to the growth control. The results of this assay, shown below in Table 6 demonstrate the antibacterial activity of the compounds of the invention.

TABLE 6

Antibacterial Activity (MIC's) of 3-Deoxyerythromycins

| MICROORGANISM | Ery A (Ref. Std) | Cmpd. of Ex. 1 | Cmpd. of Ex. 2 |
|---|---|---|---|
| STAPHYLOCOCCUS AUREUS ATCC 6538P | 0.1 | 25 | 12.5 |
| STAPHYLOCOCCUS AUREUS A5177 | 1.56 | 25 | 25 |
| STAPHYLOCOCCUS AUREUS A-5278 | >100 | >100 | >100 |
| STAPHYLOCOCCUS AUREUS CMX 642A | 0.2 | 25 | 12.5 |
| STAPHYLOCOCCUS AUREUS NCTC10649M | 0.2 | 6.2 | 12.5 |
| STAPHYLOCOCCUS AUREUS CMX 553 | 0.2 | 25 | 12.5 |
| STAPHYLOCOCCUS AUREUS 1775 | >100 | >100 | >100 |
| STAPHYLOCOCCUS EPIDERMIDIS 3519 | 0.1 | 50 | 12.5 |
| ENTEROCOCCUS FAECIUM ATCC 8043 | 0.05 | 25 | 3.1 |
| STREPTOCOCCUS BOVIS A-5169 | 0.02 | 0.78 | 0.78 |
| STREPTOCOCCUS AGALACTIAE CMX 508 | 0.02 | 3.1 | 0.78 |
| STREPTOCOCCUS PYOGENES EES61 | 0.02 | 1.56 | 0.78 |
| STREPTOCOCCUS PYOGENES 930 | >100 | >100 | >100 |
| STREPTOCOCCUS PYOGENES PIU 2548 | 6.2 | 3.1 | 0.56 |
| MICROCOCCUS LUTEUS ATCC 9341 | 0.02 | 3.1 | 1.56 |
| MICROCOCCUS LUTEUS ATCC 4698 | 0.2 | 6.2 | 3.1 |
| ESCHERICHIA COLI JUHL | 50 | >100 | >100 |
| ESCHERICHIA COLI SS | 0.2 | 0.78 | 0.78 |
| ESCHERICHIA COLI DC-2 | 100 | >100 | >100 |
| ESCHERICHIA COLI H560 | 25 | >100 | >100 |
| ESCHERICHIA COLI KNK 437 | 100 | >100 | >100 |
| ENTEROBACTER AEROGENES ATCC 13048 | >100 | >100 | >100 |
| KLEBSIELLA PNEUMONIAE ATCC 8045 | 25 | >100 | >100 |
| PROVIDENCIA STUARTII CMX 640 | >100 | >100 | >100 |
| PSEUDOMONAS AERUGINOSA BMH10 | 100 | >100 | >100 |
| PSEUDOMONAS AERUGINOSA 5007 | >100 | >100 | >100 |
| PSEUDOMONAS AERUGINOSA K799/WT | 100 | >100 | >100 |
| PSEUDOMONAS AERUGINOSA K799/61 | 1.56 | >100 | >100 |
| PSEUDOMONAS CEPACIA 2961 | >100 | >100 | >100 |
| ACINETOBACTER CALCOACETICUS CMX 669 | 12.5 | >100 | >100 |
| PSEUDOMONAS AERUGINOSA DPHD-5263 | 100 | >100 | >100 |
| PSEUDOMONAS AERUGINOSA DPHD-2862 | 100 | >100 | >100 |
| CANDIDA ALBICANS CCH 442 | >100 | >100 | >100 |
| MYCOBACTERIUM SMEGMATIS ATCC 114 | 25 | 100 | 6.2 |
| NOCARDIA ARSTEROIDES ATCC 9970 | 0.05 | 1.56 | 0.02 |

| MICROORGANISM | Cmpd. of Ex. 3 | Cmpd. of Ex. 4 | Cmpd. of Ex. 5 |
|---|---|---|---|
| STAPHYLOCOCCUS AUREUS ATCC 6538P | 6.2 | 1.56 | 12.5 |
| STAPHYLOCOCCUS AUREUS A5177 | 3.1 | 1.56 | 6.2 |
| STAPHYLOCOCCUS AUREUS A-5278 | >100 | 50 | 25 |
| STAPHYLOCOCCUS AUREUS CMX 642A | 3.1 | 1.56 | 12.5 |
| STAPHYLOCOCCUS AUREUS NCTC10649M | 6.2 | 1.56 | 6.2 |
| STAPHYLOCOCCUS AUREUS CMX 553 | 3.1 | 1.56 | 6.2 |
| STAPHYLOCOCCUS AUREUS 1775 | >100 | 50 | 25 |
| STAPHYLOCOCCUS EPIDERMIDIS 3519 | 6.2 | 1.56 | 12.5 |
| ENTEROCOCCUS FAECIUM ATCC 8043 | 0.78 | 0.39 | 1.56 |
| STREPTOCOCCUS BOVIS A-5169 | 0.2 | 0.02 | 1.56 |
| STREPTOCOCCUS AGALACTIAE CMX 508 | 0.2 | 0.1 | 1.56 |
| STREPTOCOCCUS PYOGENES EES61 | 0.2 | 0.05 | 1.56 |
| STREPTOCOCCUS PYOGENES 930 | >100 | 6.2 | 6.2 |
| STREPTOCOCCUS PYOGENES PIU 2548 | 0.78 | 0.2 | 3.1 |
| MICROCOCCUS LUTEUS ATCC 9341 | 0.78 | 1.56 | 3.1 |
| MICROCOCCUS LUTEUS ATCC 4698 | 0.78 | 1.56 | 1.56 |
| ESCHERICHIA COLI JUHL | >100 | >100 | |
| ESCHERICHIA COLI SS | 0.78 | 1.56 | |
| ESCHERICHIA COLI DC-2 | >100 | 50 | 12.5 |
| ESCHERICHIA COLI H560 | >100 | 25 | >100 |
| ESCHERICHIA COLI KNK 437 | >100 | >100 | >100 |
| ENTEROBACTER AEROGENES ATCC 13048 | >100 | >100 | >100 |
| KLEBSIELLA PNEUMONIAE ATCC 8045 | >100 | >100 | >100 |
| PROVIDENCIA STUARTII CMX 640 | >100 | >100 | >100 |
| PSEUDOMONAS AERUGINOSA BMH10 | >100 | >100 | >100 |
| PSEUDOMONAS AERUGINOSA 5007 | >100 | >100 | >100 |
| PSEUDOMONAS AERUGINOSA K799/WT | >100 | 100 | >100 |
| PSEUDOMONAS AERUGINOSA K799/61 | >100 | 12.5 | >100 |
| PSEUDOMONAS CEPACIA 2961 | >100 | | 100 |
| ACINETOBACTER CALCOACETICUS CMX 669 | >100 | 100 | >100 |
| PSEUDOMONAS AERUGINOSA DPHD-5263 | >100 | 100 | >100 |
| PSEUDOMONAS AERUGINOSA DPHD-2862 | >100 | >100 | >100 |
| CANDIDA ALBICANS CCH 442 | >100 | 100 | 100 |
| MYCOBACTERIUM SMEGMATIS ATCC 114 | 3.1 | 1.56 | 3.1 |
| NOCARDIA ARSTEROIDES ATCC 9970 | 0.2 | 3.1 | 3.1 |

| MICROORGANISM | Cmpd. of Ex. 6 | Cmpd. of Ex. 8 |
|---|---|---|
| STAPHYLOCOCCUS AUREUS ATCC 6538P | 6.2 | 0.1 |
| STAPHYLOCOCCUS AUREUS A5177 | 6.2 | 1.56 |
| STAPHYLOCOCCUS AUREUS A-5278 | >100 | >100 |
| STAPHYLOCOCCUS AUREUS CMX 642A | 6.2 | 0.2 |
| STAPHYLOCOCCUS AUREUS NCTC10649M | 6.2 | 0.2 |
| STAPHYLOCOCCUS AUREUS CMX 553 | 6.2 | 0.2 |
| STAPHYLOCOCCUS AUREUS 1775 | >100 | >100 |
| STAPHYLOCOCCUS EPIDERMIDIS 3519 | 12.5 | 0.1 |
| ENTEROCOCCUS FAECIUM ATCC 8043 | 0.78 | 0.05 |
| STREPTOCOCCUS BOVIS A-5169 | 0.39 | 0.02 |
| STREPTOCOCCUS AGALACTIAE CMX 508 | 0.39 | 0.02 |
| STREPTOCOCCUS PYOGENES EES61 | 0.39 | 0.02 |
| STREPTOCOCCUS PYOGENES 930 | >100 | >100 |
| STREPTOCOCCUS PYOGENES PIU 2548 | 0.78 | 6.2 |
| MICROCOCCUS LUTEUS ATCC 9341 | 0.39 | 0.02 |
| MICROCOCCUS LUTEUS ATCC 4698 | 0.39 | 0.2 |
| ESCHERICHIA COLI JUHL | | 50 |
| ESCHERICHIA COLI SS | | 0.2 |
| ESCHERICHIA COLI DC-2 | 0.78 | 100 |
| ESCHERICHIA COLI H560 | 50 | 25 |
| ESCHERICHIA COLI KNK 437 | 25 | 100 |
| ENTEROBACTER AEROGENES ATCC 13048 | >100 | >100 |

TABLE 6-continued

| Antibacterial Activity (MIC's) of 3-Deoxyerythromycins | | |
|---|---|---|
| KLEBSIELLA PNEUMONIAE ATCC 8045 | >100 | 25 |
| PROVIDENCIA STUARTII CMX 640 | 100 | >100 |
| PSEUDOMONAS AERUGINOSA BMH10 | >100 | 100 |
| PSEUDOMONAS AERUGINOSA 5007 | >100 | >100 |
| PSEUDOMONAS AERUGINOSA K799/WT | >100 | 100 |
| PSEUDOMONAS AERUGINOSA K799/61 | >100 | 1.56 |
| PSEUDOMONAS CEPACIA 2961 | 12.5 | >100 |
| ACINETOBACTER CALCOACETICUS CMX 669 | >100 | 12.5 |
| PSEUDOMONAS AERUGINOSA DPHD-5263 | 50 | 100 |
| PSEUDOMONAS AERUGINOSA DPHD-2862 | >100 | 100 |
| CANDIDA ALBICANS CCH 442 | >100 | >100 |
| MYCOBACTERIUM SMEGMATIS ATCC 114 | 3.1 | 25 |
| NOCARDIA ARSTEROIDES ATCC 9970 | 0.78 | 0.05 |

What is claimed is:

1. A compound, or a pharmaceutically acceptable salt or ester thereof, having a formula selected from the group consisting of:

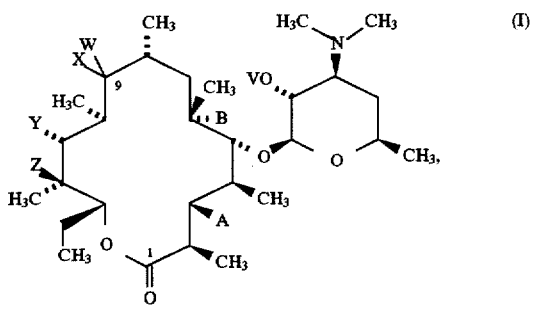

wherein:

A is hydrogen, —O(C=S)—SR$^1$, or —O(C=S)—OR$^1$, wherein R$^1$ is selected from the group consisting of:
  (a) $C_1$–$C_6$-alkyl,
  (b) aryl-$C_1$–$C_6$-alkyl,
  (c) substituted aryl-$C_1$–$C_6$-alkyl,
  (d) aryl, and
  (e) heteroaryl;

B is hydrogen, hydroxy, or methoxy;

V is hydrogen or a hydroxy-protecting group;

W is hydrogen; and X is selected from the group consisting of:
  (a) NR$^2$R$^3$, wherein R$^2$ and R$^3$ are independently selected from the group consisting of hydrogen, $C_1$–$C_6$-alkyl, $C_1$–$C_6$-alkylamino, aryl-$C_1$–$C_6$-alkyl or heteroaryl-$C_1$–$C_6$-alkyl, or wherein R$^2$ and R$^3$ are taken together with the nitrogen atom to which they are attached to form a 5-to-7-membered saturated ring; and
  (b) NR4—(C=O)—R$^1$, wherein R$^1$ is as described above and R$^4$ is hydrogen or $C_1$–$C_6$-alkyl; or W and X are taken together and represent =O, =N—O—R$^2$, wherein R$^2$ is as described above, or =N—R$^5$, wherein R$^5$ is selected from the group consisting of:
  (a) hydrogen,
  (b) $C_1$–$C_6$-alkyl,
  (c) substituted $C_1$–$C_6$-alkyl,
  (d) —(CH$_2$)$_m$—L—(CH$_2$)$_n$—M—CH$_2$—H, wherein m=1–6, n=1–6, L and M are both oxygen, L is oxygen and M is absent, or M is oxygen and L is absent,
  (e) —(CH$_2$)$_m$—L-aryl-M—(CH$_2$)$_n$—H, wherein m=1–6, n=1–6, L and M are both oxygen, L is oxygen and M is absent, or M is oxygen and L is absent, and
  (f) —(CH$_2$)$_m$L—(CH$_2$)$_n$—M-aryl-H, wherein m=1–6, n=1–6, L and M are both oxygen, L is oxygen and M is absent, or M is oxygen and L is absent;

Y is —OH, or —OR$^6$ wherein R$^6$ is a hydroxy-protecting group; and

Z is hydrogen, —OH, or —OR$^7$ wherein R$^7$ is a hydroxy-protecting group;

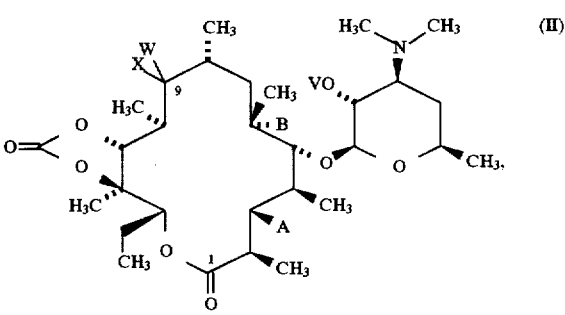

wherein A, B, V, W and X are as defined above; and

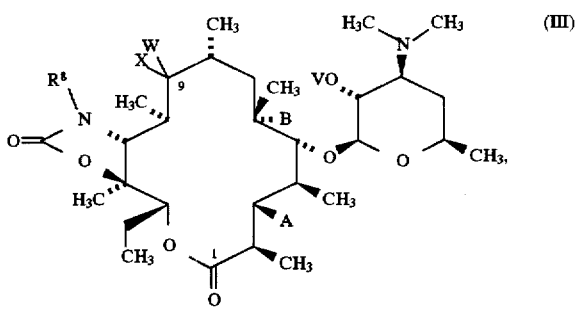

wherein A, B, V, W, and X are as defined above, and R$^8$ is selected from the group consisting of:
  (a) hydrogen,
  (b) $C_1$–$C_6$-alkyl,
  (c) aryl,
  (d) aryl-$C_1$–$C_6$-alkyl,
  (e) heteroaryl-$C_1$–$C_6$-alkyl,
  (f) cycloalkyl,
  (g) cycloalkyl-$C_1$–$C_6$-alkyl,
  (h) —NH—R$^9$, wherein R$^9$ is selected from the group consisting of:
    (aa) $C_1$–$C_6$-alkyl,
    (bb) aryl-$C_1$–$C_6$-alkyl,
    (cc) heteroaryl-$C_1$–$C_6$-alkyl,
    (dd) $C_3$–$C_7$-cycloalkyl,
    (ee) $C_3$–$C_7$-cycloalkyl-$C_1$–$C_6$-alkyl,
    (ff) —CO—$C_1$–$C_6$-alkyl,
    (gg) —CO-aryl, and
    (hh) —CO—$C_1$–$C_6$-alkyl-aryl-; and
  (i) —N=CH—R$^{10}$, wherein R$^{10}$ is selected from the group consisting of:
    (aa) $C_1$–$C_6$-alkyl,
    (bb) aryl,
    (cc) aryl-$C_1$–$C_6$-alkyl,
    (dd) heteroaryl-$C_1$–$C_6$-alkyl,
    (ee) $C_3$–$C_7$-cycloalkyl, and
    (ff) $C_3$–$C_7$-cycloalkyl-$C_1$–$C_6$-alkyl.

2. A compound according to claim 1 having the formula I.

3. A compound according to claim 2 wherein A and Z are hydrogen, Y is O—R$^6$, wherein R$^6$ is hydrogen or a hydroxy-protecting group.

4. A compound according to claim 2 wherein A is hydrogen and Z is O—$R^7$.

5. A compound according to claim 2 in which:

A=H; B=methoxy; V=H; W and X taken together are =O; Y=Z=—OH;

A=H; B=methoxy; V=H; W and X taken together are =N—OH; Y=Z=—OH;

A=H; B=methoxy; V=H; W and X taken together are =N—O—$CH_3$; Y=Z=—OH;

A=H; B=methoxy; V=H; W and X taken together are =N—O—$CH_2$—$CH_3$; Y=Z=—OH;

A=H; B=methoxy; V=H; W and X taken together are =N—O—$CH_2$—O—$CH_2$—$CH_2$—O—$CH_3$; Y=Z=—OH; or A=H; B=hydroxy; V=H; W and X taken together are =O; Y=Z=—OH.

6. A compound according to claim 1 having the formula (II).

7. A compound according to claim 6 in which: A=H; B=methoxy; V=H; W and X taken together are =O.

8. A compound according to claim 1 having the formula (III).

9. A compound according to claim 8 wherein $R^8$ is —$NHR^9$, wherein $R^9$ is selected from the group consisting of:

(a) $C_1$-$C_6$-alkyl;
(b) aryl-$C_1$-$C_6$-alkyl;
(c) heteroaryl-$C_1$-$C_6$-alkyl;
(d) $C_3$-$C_7$-cycloalkyl;
(e) $C_3$-$C_7$-cycloalkyl-$C_1$-$C_6$-alkyl;
(f) —CO—$C_1$-$C_6$-alkyl;
(g) —CO-aryl; and
(h) —CO—$C_1$-$C_6$-alkyl-aryl-.

10. A compound according to claim 9 in which:

A=H; B=methoxy; V=H; W and X taken together are =O; $R^8$=—$CH_2$—$CH_2$—$CH_2$—$CH_2$-phenyl;

A=H; B=methoxy; V=H; W and X taken together are =O; $R^8$=—$CH_2$—$CH_2$-phenyl-4-O-phenyl;

A=H; B=methoxy; V=H; W and X taken together are =O; $R^8$=$NH_2$;

A=H; B=methoxy; V=H; W and X taken together are =O; $R^8$=—NH—CO—$CH_3$;

A=H; B=methoxy; V=H; W and X taken together are =O; $R^8$=—N=CH-phenyl;

A=H; B=methoxy; V=H; W and X taken together are =O; $R^8$=—$NH_2$—$CH_2$-phenyl;

A=H; B=methoxy; V=H; W and X taken together are =O; $R^8$=—$CH_2$—$CH_2$—$CH_2$-phenyl;

A=H; B=methoxy; V=H; W and X taken together are O; $R^8$=NH—CO—$C_6H_5$;

A=H; B=methoxy; V=H; W and X taken together are O; $R^8$=NH—CO—$CH_2$—$C_6H_5$;

A=H; B=methoxy; V=H; W and X taken together are O; $R^8$=NH—CO—$CH_2CH_2C_6H_5$;

A=H; B=methoxy; V=H; W and X taken together are O; $R^8$=NH—CO—$CH_2$—$CH_2$-$C_6H_5$;

A=H; B=methoxy; V=H; W and X taken together are O; $R^8$=NH—CO—$CH_2$—COOMe;

A=H; B=methoxy; V=H; W and X taken together are O; $R^8$=NH—CO—$CH_2$—$CH_2$-(4-quinoyl);

A=H; B=methoxy; V=H; W and X taken together are O; $R^8$=N=CH—$CH_3$;

A=H; B=methoxy; V=H; W and X taken together are O; $R^8$=N=CH—$CH_2C_6H_5$;

A=H; B=methoxy; V=H; W and X taken together are O; $R^8$=N=CH—$CH_2CH_2C_6H_5$;

A=H; B=methoxy; V=H; W and X taken together are O; $R^8$=N=CH—CH=CH-phenyl;

A=H; B=methoxy; V=H; W and X taken together are O; $R^8$=N=CH—$CH_2$—$CH_2$-(4-quinoyl);

A=H; B=methoxy; V=H; W and X taken together are O; $R^8$=N=CH-cyclopentane;

A=H; B=methoxy; V=H; W and X taken together are O; $R^8$=N=CH—$CH_2$-cyclohexane;

A=H; B=methoxy; V=H; W and X taken together are O; $R^8$=NH-ethyl;

A=H; B=methoxy; V=H; W and X taken together are O; $R^8$=NH—$CH_2C_6H_5$;

A=H; B=methoxy; V=H; W and X taken together are O; $R^8$=NH—;

A=H; B=methoxy; V=H; W and X taken together are O; $R^8$=NH—$CH_2$—$CH_2$—$CH_2$—$C_6H_5$;

A=H; B=methoxy; V=H; W and X taken together are O; $R^8$=NH—$CH_2$—CH=CH-phenyl;

A=H; B=methoxy; V=H; W and X taken together are O; $R^8$=NH—$CH_2$—$CH_2$—$CH_2$-(4-quinoyl);

A=H; B=methoxy; V=H; W and X taken together are O; $R^8$=NH—CH—$CH_2$-cyclohexane;

A=H; B=methoxy; V=H; W and X taken together are O; $R^8$=H;

A=H; B=methoxy; V=H; W and X taken together are O; $R^8$=Me;

A=H; B=methoxy; V=H; W and X taken together are O; $R^8$=benzyl;

A=H; B=methoxy; V=H; W and X taken together are O; $R^8$=phenylethyl;

A=H; B=methoxy; V=H; W and X taken together are O; $R^8$=phenylpropyl;

A=H; B=methoxy; V=H; W and X taken together are O; $R^8$=—$CH_2$—$CH_2$—$CH_2$—$CH_2$-(4-quinoyl);

A=H; B=methoxy; V=H; W and X taken together are O; $R^8$=cyclohexyl;

A=H; B=methoxy; V=H; W and X taken together are O; $R^8$=—$CH_2$—$CH_2$-cyclohexyl; or A=H; B=methoxy; V=H; W and X taken together are =O; $R^8$=phenyl.

11. A pharmaceutical composition comprising a therapeutically effective amount of compound according to claim 1 in combination with a pharmaceutically acceptable carrier.

12. A method for treating bacterial infections in a patient in need of such treatment, comprising administering to the patient a therapeutically effective amount of a compound according to claim 1.

13. A process for preparing a compound having the formula:

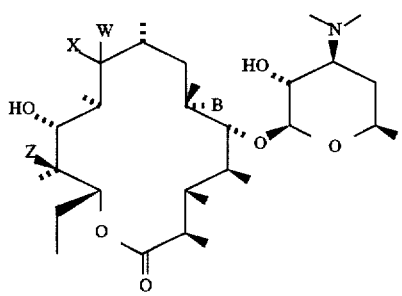

wherein

B is hydrogen, hydroxy, or methoxy;

W is hydrogen and X is selected from the group consisting of:

(a) $NR^2R^3$, wherein $R^2$ and $R^3$ are independently selected from the group consisting of hydrogen, $C_1$-$C_6$-alkyl, $C_1$-$C_6$-alkylamino, aryl-$C_1$-$C_6$-alkyl or heteroaryl-$C_1$-$C_6$-alkyl, or wherein $R^2$ and $R^3$ are taken together with the nitrogen atom to which they are attached to form a 5-to-7-membered saturated ring; and (b) $NR^4$—(C=O)—$R^1$, wherein $R^1$ is wherein $R^1$ is selected from the group consisting of (a) $C_1$-$C_6$-alkyl;

(b) aryl-$C_1$-$C_6$-alkyl;

(c) substituted aryl-$C_1$-$C_6$-alkyl;

(d) aryl; and (e) heteroaryl;

and $R^4$ is hydrogen or $C_1$-$C_6$-alkyl;

or W and X are taken together and represent =O, =N—O—$R^2$, wherein $R^2$ is as described above, or =N—$R^5$, wherein $R^5$ is selected from the group consisting of:

(a) hydrogen;

(b) $C_1$-$C_6$-alkyl;

(c) substituted $C_1$-$C_6$-alkyl;

(d) —$(CH_2)_m$—L—$(CH_2)_n$—M—$CH_2$—H, wherein m=1–6, n=1–6, L and M are both oxygen, L is oxygen and M is absent, or M is oxygen and L is absent;

(e) —$(CH_2)_m$—L-aryl-M—$(CH_2)_n$—H, wherein m=1–6, n=1–6, L and M are both oxygen, L is oxygen and M is absent, or M is oxygen and L is absent;

(f) —$(CH_2)_m$L—$(CH_2)_n$—M-aryl-H, wherein m=1–6, n=1–6, L and M are both oxygen, L is oxygen and M is absent, or M is oxygen and L is absent; and Z is hydrogen, —OH, or —$OR^7$ wherein $R^7$ is a hydroxy-protecting group; the method comprising:

(a) reacting a compound having the formula:

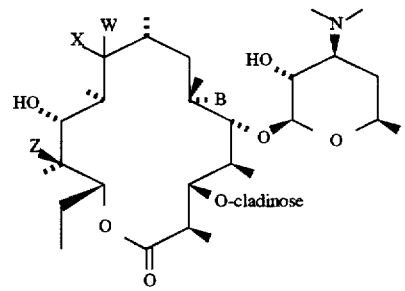

wherein B, X, W, and Z are as defined above, with an acid in a suspension in aqueous alcohol at ambient temperature, followed by basification to obtain the 3-O-descladinose compound;

(b) reducing the 3-O-descladinose compound, followed by reaction with thiophosgene and methyl iodide to obtain a compound of the formula:

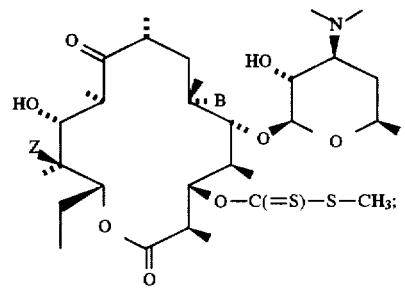

and (c) reacting the compound of step (b) with $Bu_3SnH$ under an inert atmosphere in the presence of a catalytic amount of a radical initiator, in a solvent suitable for a free radical reaction.

14. The process according to claim 13, wherein W and X taken together represent =O.

15. The process according to claim 13, wherein W and X together represent =N—O—$R^2$, wherein $R^2$ is as described above, further comprising:

(d) deoximation of the compound obtained in step (c).

16. A process for preparing a compound of the formula:

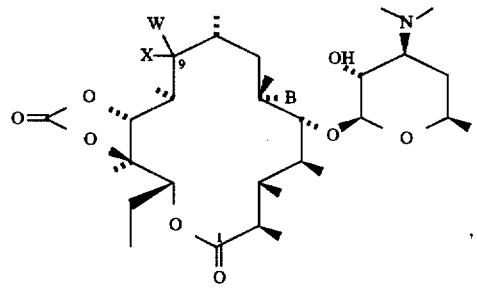

wherein

B is hydrogen, hydroxy, or methoxy;

W is hydrogen and X is selected from the group consisting of:

(a) $NR^2R^3$, wherein $R^2$ and $R^3$ are independently selected from the group consisting of hydrogen, $C_1$–$C_6$-alkyl, $C_1$–$C_6$-alkylamino, aryl-$C_1$–$C_6$-alkyl or heteroaryl-$C_1$–$C_6$-alkyl, or wherein $R^2$ and $R^3$ are taken together with the nitrogen atom to which they are attached to form a 5-to-7-membered saturated ring; and (b) $NR^4$—(C=O)—$R^1$, wherein $R^1$ is as described above and $R^4$ is hydrogen or $C_1$–$C_6$-alkyl;

or W and X are taken together and represent =O, =N—O—$R^2$, wherein $R^2$ is as described above, or =N—$R^5$, wherein $R^5$ is selected from the group consisting of:

(a) hydrogen;
(b) $C_1$–$C_6$-alkyl;
(c) substituted $C_1$–$C_6$-alkyl;
(d) —$(CH_2)_m$—L—$(CH_2)_n$—M—$CH_2$—H, wherein m=1–6, n=1–6, L and M are both oxygen, L is oxygen and M is absent, or M is oxygen and L is absent;
(e) —$(CH_2)_m$—L-aryl-M—$(CH_2)_n$—H, wherein m=1–6, n=1–6, L and M are both oxygen, L is oxygen and M is absent, or M is oxygen and L is absent;
(f) —$(CH_2)_m$L—$(CH_2)_n$—M—aryl-H, wherein m=1–6, n=1–6, L and M are both oxygen, L is oxygen and M is absent, or M is oxygen and L is absent;

the method comprising
(a) treating a compound of the formula:

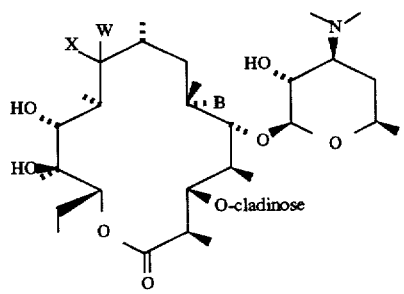

wherein B, W, and X are as defined above, with an acid in a suspension in aqueous alcohol at ambient temperature, followed by basification to obtain the 3-O-descladinose compound;

(b) protecting the 2'-hydroxy group of the 3-O-descladinose compound to obtain the compound of the formula:

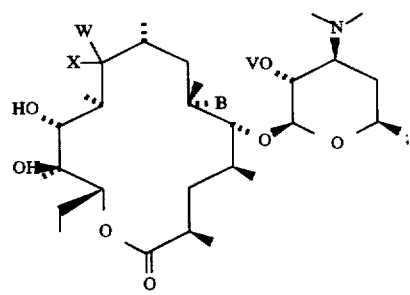

(c) reacting the compound of step (b) with a base followed by reaction with carbonyldiimidazole to obtain the compound of the formula:

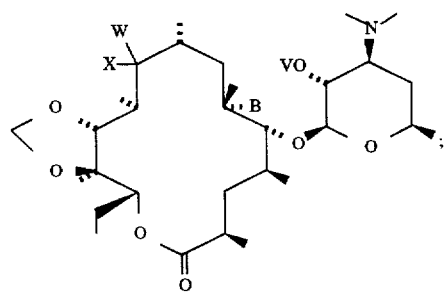

and (d) deprotecting the 2'-hydroxy group.

17. A process for preparing a compound of the formula:

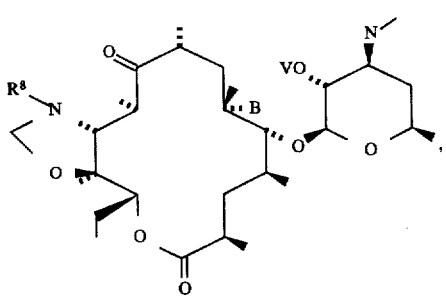

wherein

B is hydrogen, hydroxy, or methoxy;

V is hydrogen or a hydroxy-protecting group; and $R^8$ is selected from the group consisting of:

(a) hydrogen;
b) C1–C6-alkyl;
(c) aryl;
(d) aryl-C1–C6-alkyl;
(e) heteroaryl-C1–C6-alkyl;
(f) cycloalkyl;
(g) cycloalkyl-C1–C6-alkyl;
(h) —NH—$R^9$, wherein $R^9$ is selected from the group consisting of:
  (aa) C1–C6-alkyl;
  (bb) aryl-C1–C6-alkyl;
  (cc) heteroaryl-C1–C6-alkyl;
  (dd) C3–C7-cycloalkyl;
  (ee) C3–C7-cycloalkyl-C1–C6-alkyl;
  (ff) —CO—C1–C6-alkyl;
  (gg) —CO-aryl;
  (hh) —CO—C1–C6-alkyl-aryl-; and
(i) —N=CH—$R^{10}$, wherein $R^{10}$ is selected from the group consisting of:

(aa) C1–C6-alkyl;
(bb) aryl;
(cc) aryl-C1–C6-alkyl;
(dd) heteroaryl-C1–C6-alkyl;
(ee) C3–C7-cycloalkyl; and
(ff) C3–C7-cycloalkyl-C1–C6 alkyl;

the method comprising:

(a) treating a compound having the formula:

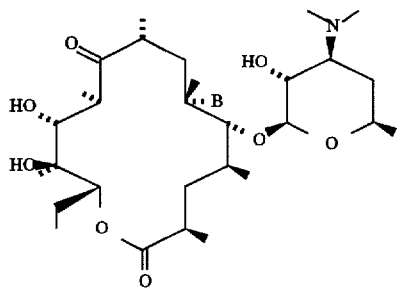

wherein B and V are as defined above, with methanesulfonyl anhydride to obtain the 2'-protected-11-mesyl compound of the formula:

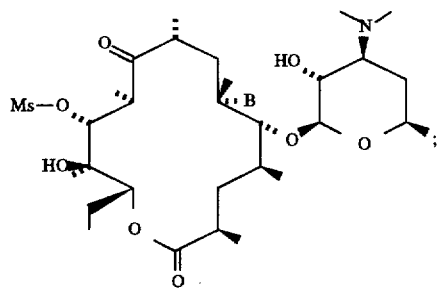

(b) reacting the compound of step (a) with sodium hexamethyldisilazide and carbonyldiimidazole to give a compound having the formula:

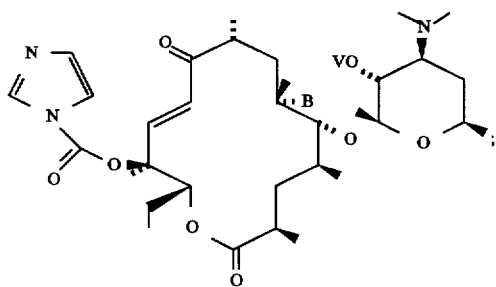

and (c) treating the compound from step (b) with a reagent selected from the group consisting of ammonia, $R^8$—$NH_2$, hydrazine, substituted hydrazine, hydroxylamine, and substituted hydroxylamine to give a compound having the formula:

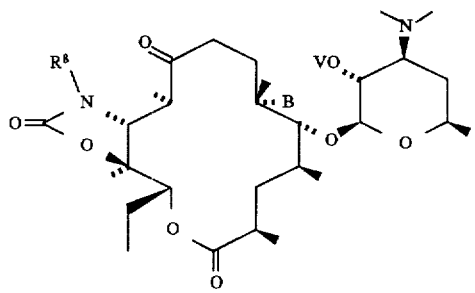

wherein $R^8$ is as defined above.

18. The process according to claim 17, comprising
(a) reacting the compound in step (b) with hydrazine in an aprotic solvent at a temperature from ambient to reflux to give the compound of the formula:

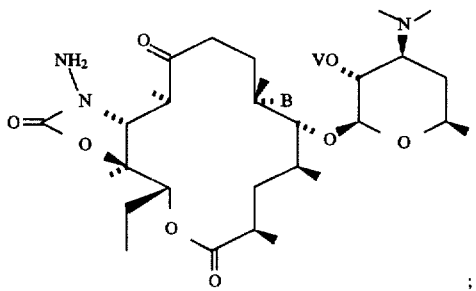

(b) optionally treating the compound from step (a) above with an aldehyde $R^9$—CHO, wherein $R^9$ as defined above to give a compound

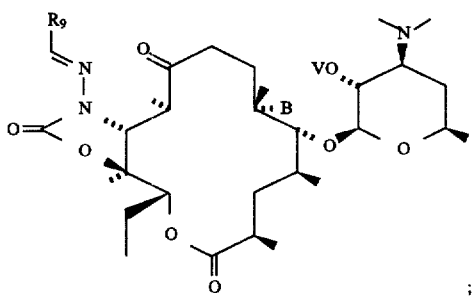

and
(c) reducing the compound in step (b) to obtain a compound of the formula:

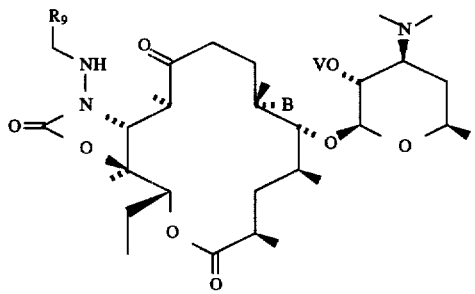

* * * * *